(12) United States Patent
Birnboim et al.

(10) Patent No.: US 9,072,499 B2
(45) Date of Patent: Jul. 7, 2015

(54) SAMPLE COLLECTION TOOL

(75) Inventors: H. Chaim Birnboim, Ottawa (CA); Roy Sunstrum, Richmond (CA); Adele Jackson, Stittsville (CA); Rafal Michal Iwasiow, Ottawa (CA); Romeo Graham, Chelsea (CA); Rod Muir, South Mountain (CA); Mike Sirois, Ottawa (CA); Michael Beach, Fitzroy-Harbour (CA); Ellen Joan MacLean, Richmond (CA); Rama Nadia Panford-Walsh, Ottawa (CA)

(73) Assignee: DNA GENOTEK INC., Kanata (CA)

( * ) Notice: Subject to any disclaimer, the term of this patent is extended or adjusted under 35 U.S.C. 154(b) by 246 days.

(21) Appl. No.: 13/637,126

(22) PCT Filed: Mar. 25, 2011

(86) PCT No.: PCT/CA2011/050159
§ 371 (c)(1),
(2), (4) Date: Jan. 16, 2013

(87) PCT Pub. No.: WO2011/116481
PCT Pub. Date: Sep. 29, 2011

(65) Prior Publication Data
US 2013/0116596 A1 May 9, 2013

Related U.S. Application Data

(60) Provisional application No. 61/318,079, filed on Mar. 26, 2010.

(51) Int. Cl.
*A61B 10/00* (2006.01)
*A61B 10/02* (2006.01)
*G01N 1/02* (2006.01)

(52) U.S. Cl.
CPC ............. *A61B 10/02* (2013.01); *A61B 10/0045* (2013.01); *A61B 2010/0216* (2013.01); *G01N 1/02* (2013.01); *G01N 2001/028* (2013.01); *A61B 10/0096* (2013.01)

(58) Field of Classification Search
USPC .................................................. 600/569, 570
See application file for complete search history.

(56) References Cited

U.S. PATENT DOCUMENTS

| 3,815,580 A | 6/1974 | Oster |
| 2007/0249961 A1 | 10/2007 | Morrison et al. |

FOREIGN PATENT DOCUMENTS

| GB | 2457654 B | 8/2009 |
| WO | WO 2007109586 A2 | 9/2007 |
| WO | WO 2010027283 A1 | 3/2010 |

OTHER PUBLICATIONS

International Search Report & Written Opinion from PCT/CA2011/050159, dated Jun. 27, 2011.

*Primary Examiner* — Brian Szmal
(74) *Attorney, Agent, or Firm* — Lathrop & Gage LLP; James H. Velema, Esq.

(57) ABSTRACT

A sample collection tool comprises a collection end configured for collecting a sample. Optionally, the sample is collected from within a body cavity of an animal without causing significant discomfort or injury to the animal. A first handle portion has a first end connected to the collection end and a second end. A second handle portion is connected to the second end of the first handle portion by a breakable connection. The second end of the first handle portion has at least one winglet. The at least one winglet is compliant in a preferential direction. The breakable connection is ruptured at least in part when the at least one winglet is forced in the preferential direction.

33 Claims, 32 Drawing Sheets

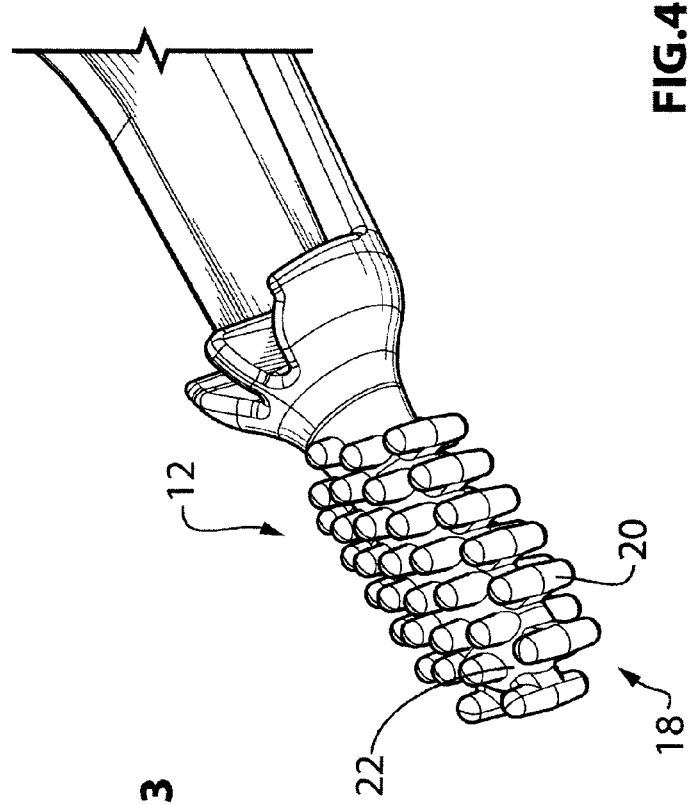
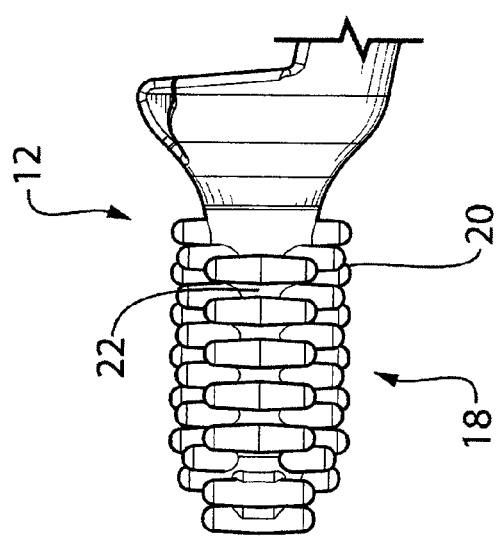

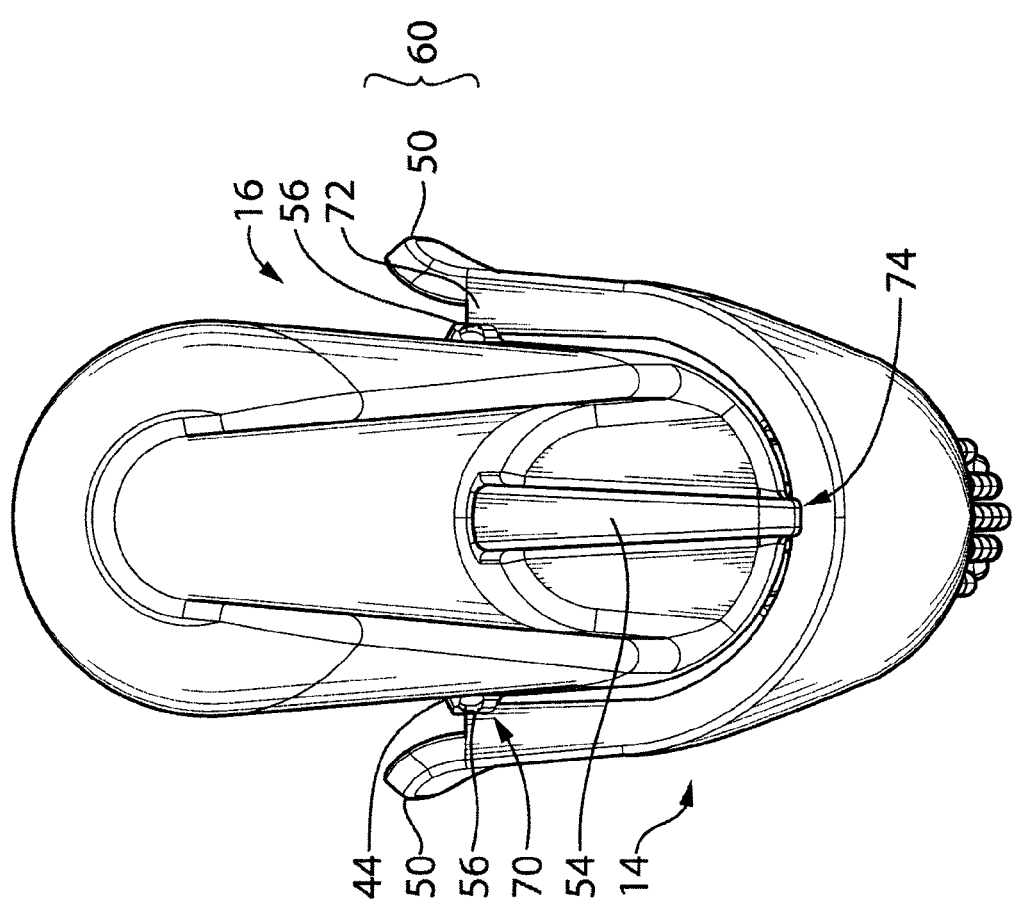

D-D

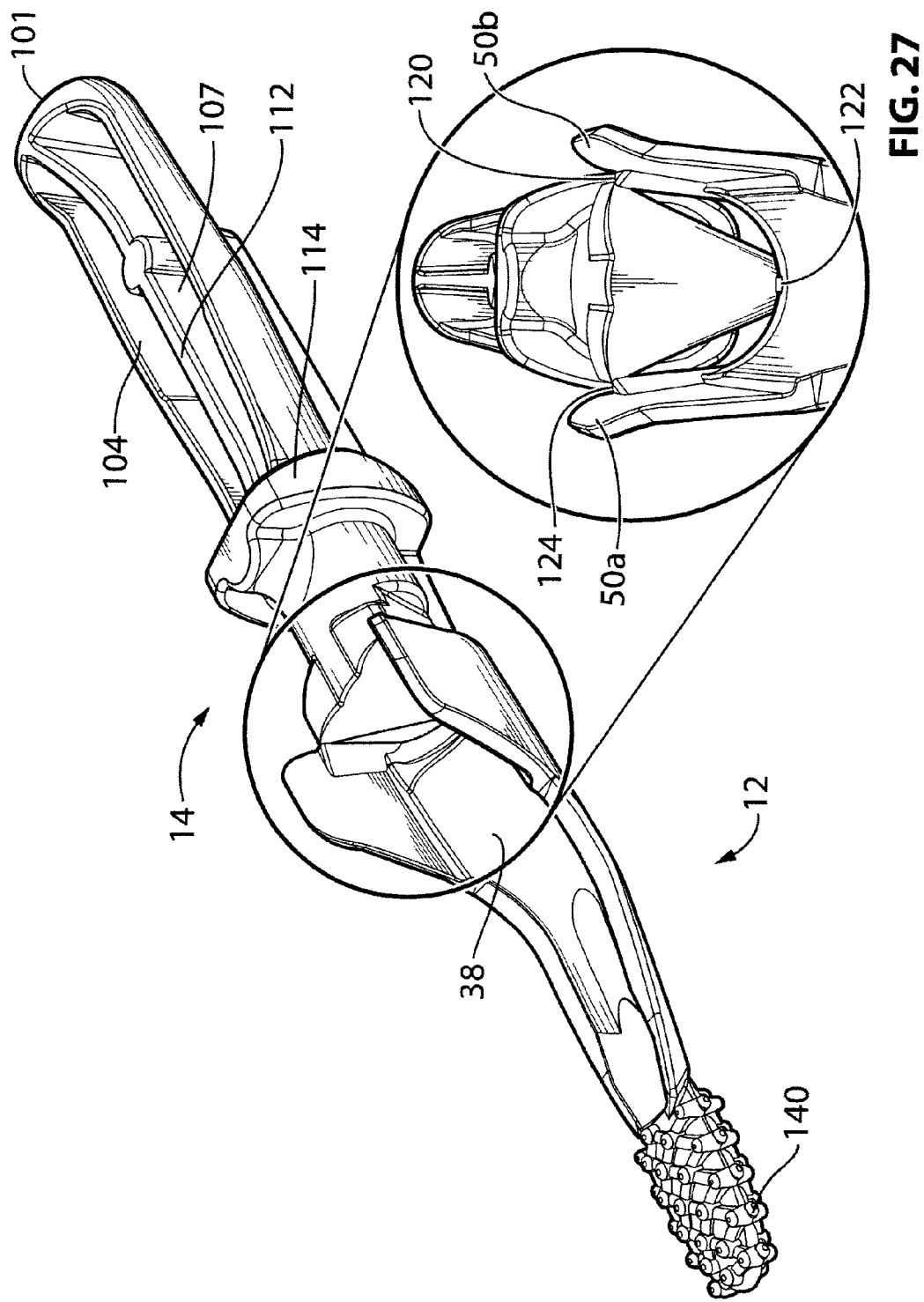

50 COLLECTORS  50 COLLECTORS  4 STRIPS (=48 TUBES)  4 STRIPS (=48 TUBES)

Total DNA yield from mouse oral collections using the sample collector tool (PA) compared to a scoop-shaped collection device (U1).

The sample collection tool is optimized for the collection from mice aged p (postnatal day) 3 to p12.

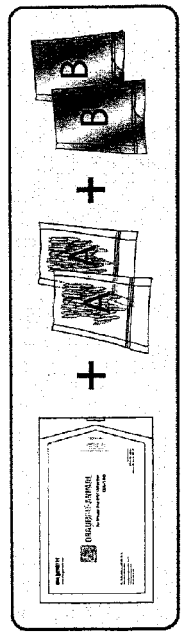
FIG. 36

FIG. 36 (cont'd)

OA-100 Collection Instructions:

Mouse Restraint for Oral Collection:

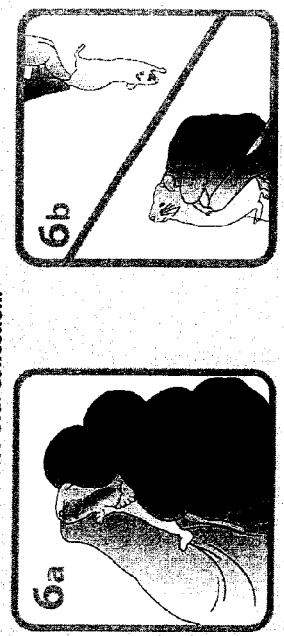

Young Pup (5-12 day old)
- Gently but firmly hold mouse as shown (figure 6a), and position in hand with thumb and forefinger on either side of pup's head at jaw level.
- NOTE: Take care not to apply significant pressure and restrict the mouse's breathing.

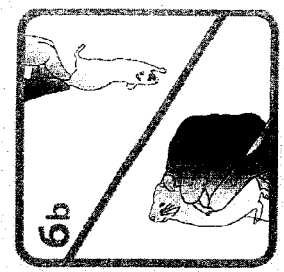

Mouse (older than 12 days)
- Remove mouse from cage by base of tail.
- Firmly grasp the loose skin over the neck/shoulder (scruff) between the thumb and forefinger.
- Restrain back end of mouse by placing tail between fourth and fifth fingers.

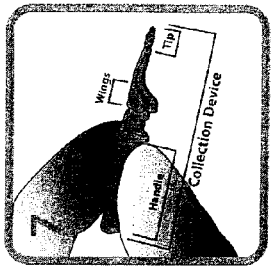

IMPORTANT: Do NOT touch collection tip to avoid contamination.
- Using thumb and index finger, pick up the collection device by the handle.
- Orient the device so thumb is on the hollow side of the handle as shown (figure 6).
- Gently insert the tip of the collection device into the mouse's mouth.

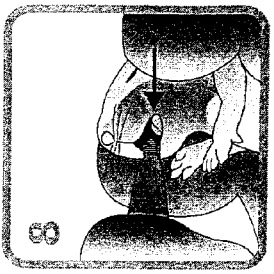

- Using the tip of the collection device, collect DNA sample by scraping the inside of the mouse's cheek pouch.
- Scrape from back to front 10 times.
- IMPORTANT: To collect a reliable DNA sample, maintain firm contact between tip and cheek at all times. Scraping pressure of the collection tip should be felt by restraining finger/thumb through the cheek.

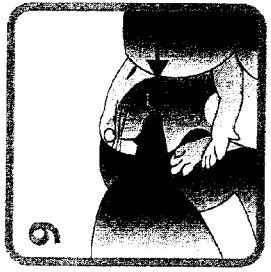

- Without removing the tip from the mouth, move the collector to the opposite cheek pouch.
- Using the other side of the tip repeat back to front scrapes 10 times to complete collection.

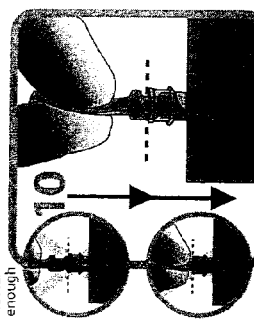

- Insert collector into sample tube in rack using a continuous downward force.
- IMPORTANT: Ensure the tip is fully seated at the bottom of the sample tube as shown (figure 9). You may hear and audible 'click' when tip is seated.

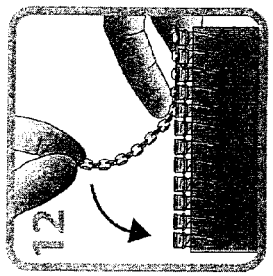

- While maintaining a downward pressure, lever the handle away from you to detach.
- Repeat step 10 if handle did not detach.
- Identify mouse (if required) and return to cage.
- Identify sample with mouse identification.
- Repeat steps 7-10 for additional mice.

- Using tube caps (set aside in step 5) tightly recap sample tubes.
- DNA sample is now stabilized at ambient temperature.

Oragene ANIMAL For Mouse Oral DNA Collection OA-100

SAMPLE COLLECTION TOOL

RELATED APPLICATIONS

This application is a 35 U.S.C. §371 filing of International Application No. PCT/CA2011/050159 filed Mar. 25, 2011, which claims priority to U.S. Provisional Patent Application No. 61/318,079, filed Mar. 26, 2010. The entire contents of each of the above documents are incorporated herein by reference.

FIELD OF THE INVENTION

This invention relates to the field of sample collection devices. More particularly, the present invention pertains to the field of detachable sample collection devices having a sample collection end with increased surface area.

BACKGROUND OF THE INVENTION

It is the usual practice to employ trained medical personnel to obtain samples and cultures for analysis from body cavities, such as the vagina, rectum, nose, sinuses, ears, mouth or throat. Typically sample collection is performed using a swab, brush, or the like.

Care must be taken in collecting a sample from the area of interest in order to avoid contamination of 1) the sample; 2) the collector of the sample; or 3) the donor of the sample. Care must also be taken to minimize the chance of injury to delicate cavity areas. However, even if trained medical personnel perform the sample collection, broad variability in sample quality and yield and in reproducibility is observed when currently available sample collection devices are employed. Furthermore, sample collection devices currently in use are not typically adaptable for use in collecting samples from small subjects, such as neonatal laboratory animals.

Obtaining cells from neonatal rodents is critical for investigations involving genetically-modified (e.g., transgenic and knockout) mice and rats. Various practices exist for obtaining cells from animals for DNA genotyping. For example, common practices used to acquire cells from a neonatal mouse for DNA genotyping involve total or partial amputation of the rodent's toe, ear or tail. These practices are both invasive and mutilating, and toe clipping has been generally banned.

In response to these practices, mice exhibit responses to pain that may include one or more specific behaviours such as vocalizing, biting and avoidance (running away). Neonatal mice contort and move their entire bodies back and forth in response to tail clipping, showing that they experience significant pain. Following amputation of tail tissue, some mice bleed to death or succumb to cannibalization.

Non-invasive and painless buccal cell isolation methods involving saliva, mouthwash, treated filter paper, cytobrush and foam or cotton-tip swabs are available for collecting buccal cells from humans for diagnostic analyses. These methods, however, are extremely difficult, if not impossible, to adapt for the small size of, for example, the neonatal and juvenile mouse. For example, the filter paper on the Bode Buccal DNA collector is about the width of a neonatal mouse head. The Oragene®•DNA Self Collection Kit (DNA Genotek Inc.) requires 1-2 ml of human saliva sample to extract sufficient DNA for processing, or approximately the total weight of the 1 g neonatal mouse. Traditional cotton swabs are much too large to collect buccal cells from the neonatal mouse and would have the potential to suffocate the mouse if forced into the mouth. Although comparison of cytobrush, mouthwash and treated card for obtaining human buccal cells found that the cytobrush was the best method for human sampling, these approaches cannot be adapted directly to mice, especially day of life 1-15 mice. A serrated pipette tip used to collect human cells for RNA isolation is too abrasive for the fragile neonatal mouse cheek. Mouse pups require methods of handling that minimize pain and stress, since they are very fragile and can die easily during execution of the experimental protocol, succumb to cannibalization by the dam following the sampling, or succumb to starvation following rejection by the dam.

Protocols have been developed to address minimally invasive and painless mouse buccal cell sampling. One method for sampling and extraction of mouse DNA used a cotton swab adapted for adult, but not neonatal, mice. A common toothpick, though more appropriate in size, would lack a reservoir for collecting adequate buccal cells from the newborn mouse for subsequent analyses. Kits involving a buccal brush or swab (Epicentre), mouse saliva (10 µL; Sigma), and buccal cells applied on a card with a swab (Whatman) are examples of commercial products available for adult mice. However, the youngest mouse described in the protocols for these products was 1 month old. Due to alterations in their genotype, it is not uncommon for knockout and transgenic mice to die within this time frame. The present invention and method allows for early sampling of genetic material from neonatal mice, enabling researchers to identify and possibly treat transgenic and knockout mice within their first few days of life.

Recently, a scoop-shaped tool has been developed for sample collection from the mouth of a neonatal mouse (Zhang et al., WO 2007/109586 A2 and US 2009/0075289). While the scoop-shaped tool addresses some of the problems of the past, sample collection using this scoop requires technical skill in order to obtain reproducibly good quality samples.

Other sample collection devices are described in US2007/0249961 and US2003/0181826, for example.

To date, known, standardized, relatively non-invasive methods for buccal cell sampling from neonatal mice are not available from commercial sources or disclosed in published literature.

Therefore, there remains a need for a non-invasive, non-mutilating approach to obtain cells and biomolecules from animals, such as neonatal mice, for experimental procedures that require an oral sample, such as buccal cell sampling, for example for DNA extraction and genotyping, RNA expression analysis, detection of disease or detection of an infectious agent (e.g., virus, bacteria, fungus).

Furthermore, there remains a need for a sample collection tool that requires only minimal technical skill to obtain reproducibly good sample quality from body cavities, such as the vagina, rectum, nose, sinus, ears, mouth or throat. Good sample quality is generally determined by a sufficient, reproducible yield of biomolecules, such as nucleic acids and proteins, to readily permit downstream analysis. Such a tool would ideally also be amenable for use with standard collection and analysis containers and tools, such as sample collection receptacles, assay tubes and pipettes.

SUMMARY

It is an object of the present invention to ameliorate at least some of the inconveniences and drawbacks mentioned above by providing a sample collection tool that provides ease of use and reproducible sample quality.

In accordance with one aspect, there is provided a collection tool having a collection end and a handle end, wherein the collection end comprises an approximately spherical, ovoid or ellipsoid tip that has a plurality of raised sampling elements extending outwardly from said tip. Optionally, the collection end is also sized and shaped to fit within a body cavity of an animal for sample collection without causing injury or significant discomfort.

In accordance with one embodiment, the plurality of raised sampling elements is a plurality of protuberances projecting radially outwardly from all or a portion of the tip.

In accordance with an alternative embodiment, the plurality of raised sampling elements is a plurality of panels extending radially outwardly from all or a portion of the tip.

In accordance with another alternative embodiment, the plurality of raised sampling elements is a lattice of intersecting ridges extending radially outwardly from all or a portion of the tip and having one or more discrete protrusions further extending outwardly therefrom.

In accordance with another alternative embodiment, the plurality of raised sampling elements are ridges extending radially outwardly from all or a portion of the tip and forming a series of parallel-spaced rings comprising one or more discrete protrusions further extending outwardly therefrom.

In accordance with another aspect, there is provided a collection tool having a collection end configured for collecting a sample from a cavity of an animal; a first handle portion having a first end connected to the collection end and a second end; and a second handle portion connected to the second end of the first handle portion by a breakable connection, the second end of the first handle portion having at least one winglet, the at least one winglet being compliant in a preferential direction, the breakable connection being ruptured at least in part when the at least one winglet is forced in the preferential direction. Optionally, a plurality of breakable connections (such as two, three, four or more than four connections, for example) are incorporated between the first handle portion and second handle portion.

In accordance with one embodiment, the first handle portion and the collection end are sized and shaped to fit inside a sample receptacle, such as a microcentrifuge or polymerase chain reaction (PCR) tube, as commonly used in the industry. Optionally, the collection tool has a hollow portion adapted to receive a pipette tip as commonly used in the industry. Ideally, the first handle portion and collection end are detachable from the second handle portion of the tool.

Advantageously, the detached first handle portion and collection end containing the collected sample can remain in the sample receptacle. Optionally, the sample receptacle can contain one or more liquid, solid, or semi-solid compositions, such as a stabilizing, preserving, neutralizing or transport solution. Ideally, the receptacle can be closed (such as by capping or screwing a lid on the receptacle, for example). The contained composition(s) can be used, for example, for extracting biomolecules from the sample to prepare the sample for downstream analysis, such as amplification and/or hybridization analysis.

In accordance with another aspect, there is provided a sample collection kit, comprising a sample collection tool as described herein, and a receptacle for receiving the sample collection tool following collection of a sample. Optionally, the kit can comprise a container comprising a composition for preserving the sample when the solution and the sample are mixed in the receptacle. Further, a protease, such as proteinase K, can be present in the kit. The protease can be dried and suitable for reconstitution in the composition and/or sample. The dried protease can be adhered to the tool or to the receptacle, for example. It is contemplated that one or more other reagents, and in particular one or more other dried reagents, can also be present in the kit.

The composition in the kit can comprise a nucleic-acid preserving composition, such as a DNA-preserving solution. Alternatively, the kit can have a composition comprising a reagent for extracting a nucleic acid from the sample, a stabilizing composition, a fixative, a composition for preparing the sample for further analysis, a decontaminant, a disinfectant, a composition for facilitating transport of the sample, or a combination thereof. The composition can be a PCR reagent which can be used to prepare the sample for PCR. In one embodiment, the PCR reagent comprises KCl, Triton X-100, bovine serum albumin (BSA), and $MgCl_2$.

Embodiments of the present invention each have at least one of the above-mentioned objects and/or aspects, but do not necessarily have all of them. It should be understood that some aspects of the present invention that have resulted from attempting to attain the above-mentioned objects may not satisfy these objects and/or may satisfy other objects not specifically recited herein.

Additional and/or alternative features, aspects, and advantages of embodiments will become apparent from the following description, the accompanying drawings, and the appended claims.

BRIEF DESCRIPTION OF THE DRAWINGS

For a better understanding of the present invention, as well as other aspects and further features thereof, reference is made to the following description which is to be used in conjunction with the accompanying drawings, where:

FIG. 3 is a side elevation view of a collection end of the sample collection tool of FIG. 1;

FIG. 4 is a front, top, right perspective view of the collection end of the sample collection tool of FIG. 3.

FIG. 9 is an enlarged view of an element of the sample collecting tool of FIG. 1 showing a breakable connection between two handle portions;

FIG. 27 shows a bottom view of the sample collection tool of FIG. 26.

FIG. 36 illustrates instructions for use of the sample collection device according to one embodiment.

DETAILED DESCRIPTION OF THE PREFERRED EMBODIMENTS

Figure 1:
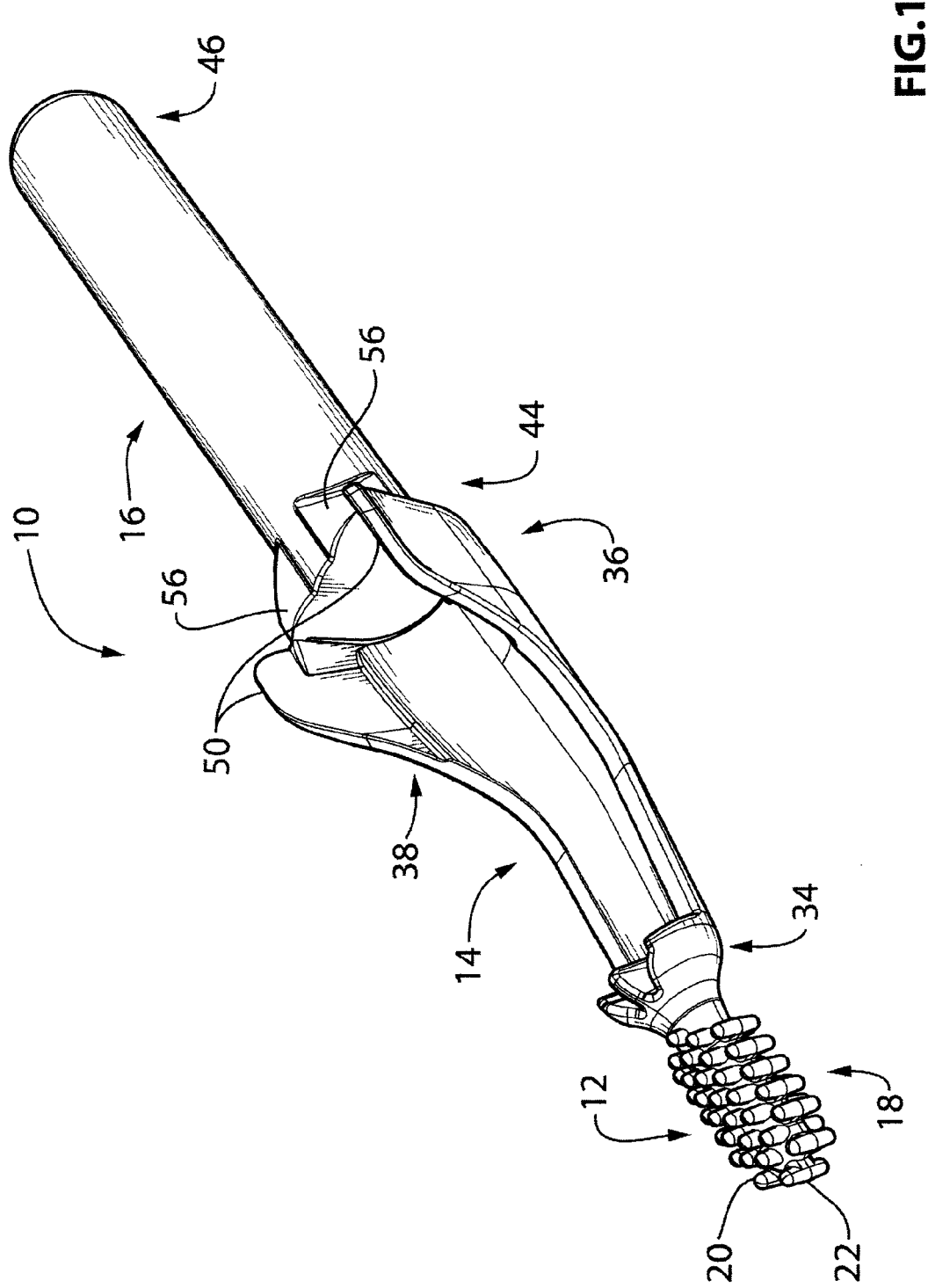
FIG. 1 is a front, left perspective view of a sample collecting tool according to one embodiment.

Unless defined otherwise, all technical and scientific terms used herein have the same meaning as commonly understood by one of ordinary skill in the art to which this invention belongs.

Unless the context clearly indicates otherwise, as used herein plural forms of the terms herein are to be construed as including the singular form and vice versa.

The terms "comprises" and "comprising" as used herein will be understood to mean that the list following is non-exhaustive and may or may not include any other additional suitable items, for example one or more further feature(s), component(s) and/or ingredient(s) as appropriate.

For the purpose of this application, the term "sample", as used herein, includes, but is not limited to, samples obtained from within a body cavity of an animal, such as the vagina, rectum, nose, sinuses, ears, mouth or throat. Such samples contain one or more of saliva, sputum, mucus, blood, pus, wax, microorganisms (including viral, bacterial, fungal, protozoan, parasitic, single-celled, and/or multi-cellular organisms) present in the body cavity, cells (such as, but not limited to, buccal/epithelial cells and immune cells), buccal mucosa, pharyngeal, nasal/nasal pharyngeal and sinus secretions, mucous, feces, semen/sperm, products of menstruation, cervical secretions and vaginal fluid/secretions. "Sample" also includes, but is not limited to, samples obtained from foodstuff, tissue, geological samples, potentially contaminated (e.g., by biological agents, radioactive isotopes, etc.) substances and surfaces. A sample, as used herein, can comprise a biomolecule, such as a nucleic acid (including DNA and/or RNA), a protein, or a prion, for example.

The term "sputum", as used herein, refers to mucoid matter contained in or discharged from the nasal or oral cavity of a mammal, including saliva and discharges from the respiratory passages, including the lungs.

The term "saliva", as used therein, refers to the secretion, or combination of secretions in the mouth, from any of the salivary glands, including the parotid, submaxillary, and sublingual glands, optionally mixed with the secretions from the numerous small labial, buccal, and palatal glands that line the mouth. The term "saliva" can also refer to a mixture of said secretion (or combination of secretions in the mouth) with any other sample as defined herein derived from any other source.

The term "solution", as used herein, typically refers to a liquid medium, and more typically solutions which are liquid at room temperature. However, it would be understood that other media may be contemplated, such as gels or semi-solids, which may have a melting point above room temperature and which take the form of a liquid medium once melted.

The sample collection tool of the present invention includes a handle portion and a sample collection portion. It is designed for facile and reproducible sample collection as well as for convenient transfer of the collected sample to a sample collection, storage or assay receptacle. In particular, the sample collection portion of the collection tool of the present invention includes a sample gathering tip portion that is sized and shaped to fit within a standard sample collection or storage receptacle. Advantageously, the sample collection tool can also be designed such that the main handle portion is detachable from the sample collection portion to allow the entire sample collection portion to be retained within a sample collection, storage or assay receptacle. Optionally, the receptacle may contain a stabilizing solution for preserving the sample and extracting the biomolecules of interest.

The sample collection portion of the collection tool of the present invention includes an approximately ovoid, spherical or ellipsoid tip that includes a plurality of raised sampling elements. The inventors have found improved sample collection yield and reproducibility results from increasing the sampling surface area of the collection tool, in comparison to that of standard collection swabs. The sampling surface area is increased by including the plurality raised sampling elements over the surface of the approximately ovoid, spherical or ellipsoid tip. The sampling elements can be in the form of rigid, semi-rigid or flexible bristle-like protrusions, or stubs, ridges with alternating valleys, bumps and depressions, or any other pattern that increases the sampling surface area and, consequently increases the overall sample collection yield. The inventors have also found that the sample can be left to dry on the sample collection portion or/and deposited into an empty collection tube and stored under ambient conditions. After several days to a week, the collected sample is readily released from the collection end with the addition of a liquid reagent. Thus, the sample collection portion of the present invention is particularly advantageous over other tools such as standard collection swabs, brushes and sponges. Biomolecules, particularly DNA, can adhere tightly to cotton fibres of swabs and can become trapped within brushes and sponges. By contrast, the inventors have found that the collected sample is readily released from the sample collection end of the collection tool present invention and is, thus, suitable for downstream analysis.

The present invention will be described in greater detail with respect to a specific example in which the collection tool is sized for sample collection from the mouth of a mouse of first or second day of life (DOL). However, it should be understood that the collection tool of the present invention is suitable and scalable for sample collection from juvenile and adult mice, as well as other animals, such as neonatal and non-neonatal laboratory animals (mice, rats, hamster and rabbits) and domestic animals, and humans. Furthermore, although the present application has been written to focus on the use of the collection tool in obtaining samples from body cavities, it should be appreciated that the collection tool will have much broader application. In particular, the present sample collection tool will be useful at least in collecting any sample that can be obtained using, for example, currently available sample collection swabs, brushes, sticks and the like.

One possible advantage of the present invention and method is that it may allow for early sampling of genetic material from neonatal mice, enabling researchers to identify and possibly treat transgenic and knockout mice within their first few days of life.

Figure 2:
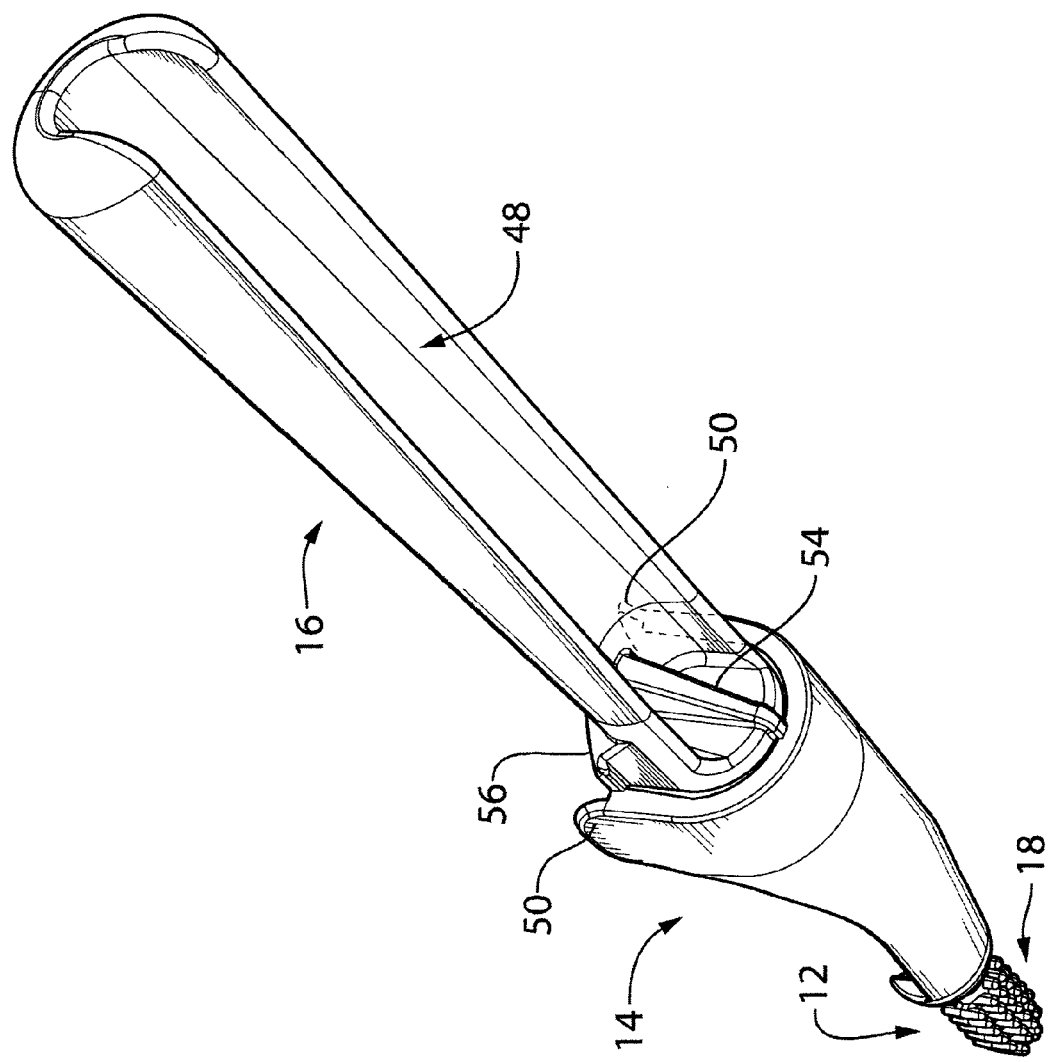
FIG. 2 is a rear, bottom, left perspective view of the sample collecting tool of FIG. 1.
Figure 8:
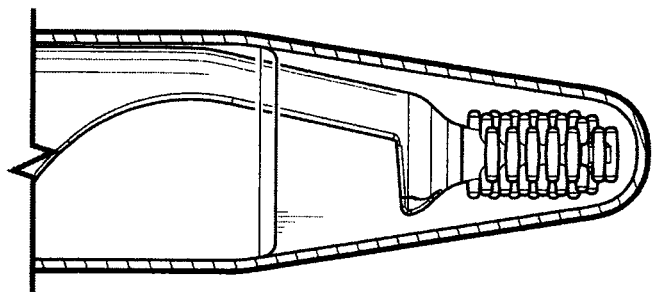
FIG. 8 is a side elevation view of FIG. 7.
Figure 7:
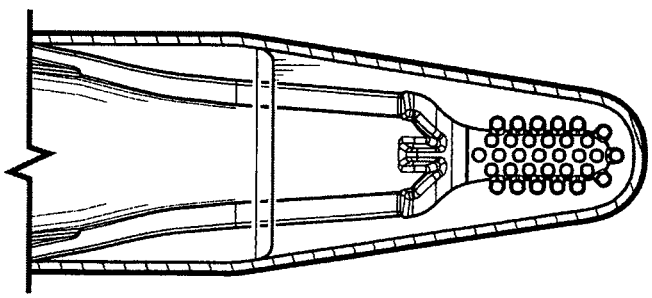
FIG. 7 is a front elevation view of a portion of the sample collection tool of FIG. 1 with a zone (dashed) used to receive a dried reagent.
Figure 6:
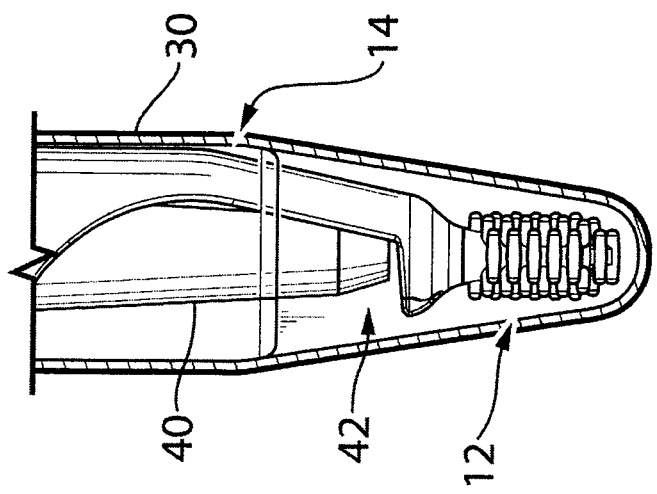
FIG. 6 is a side elevation view of a portion of the sample collection tool of FIG. 1 inside an microcentrifuge tube with a pipette in broken lines inserted in the sample collection tool.
Figure 10:
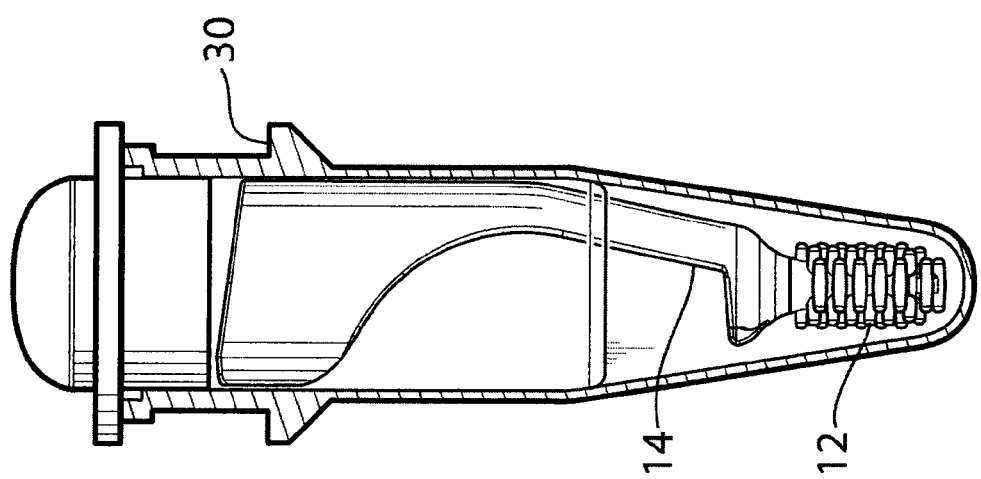
FIG. 10 is a side elevation view of a portion of the sample collection tool of FIG. 1 separated from the rest of the sample collection tool and encapsulated in a PCR or microcentrifuge tube.
Figure 11:
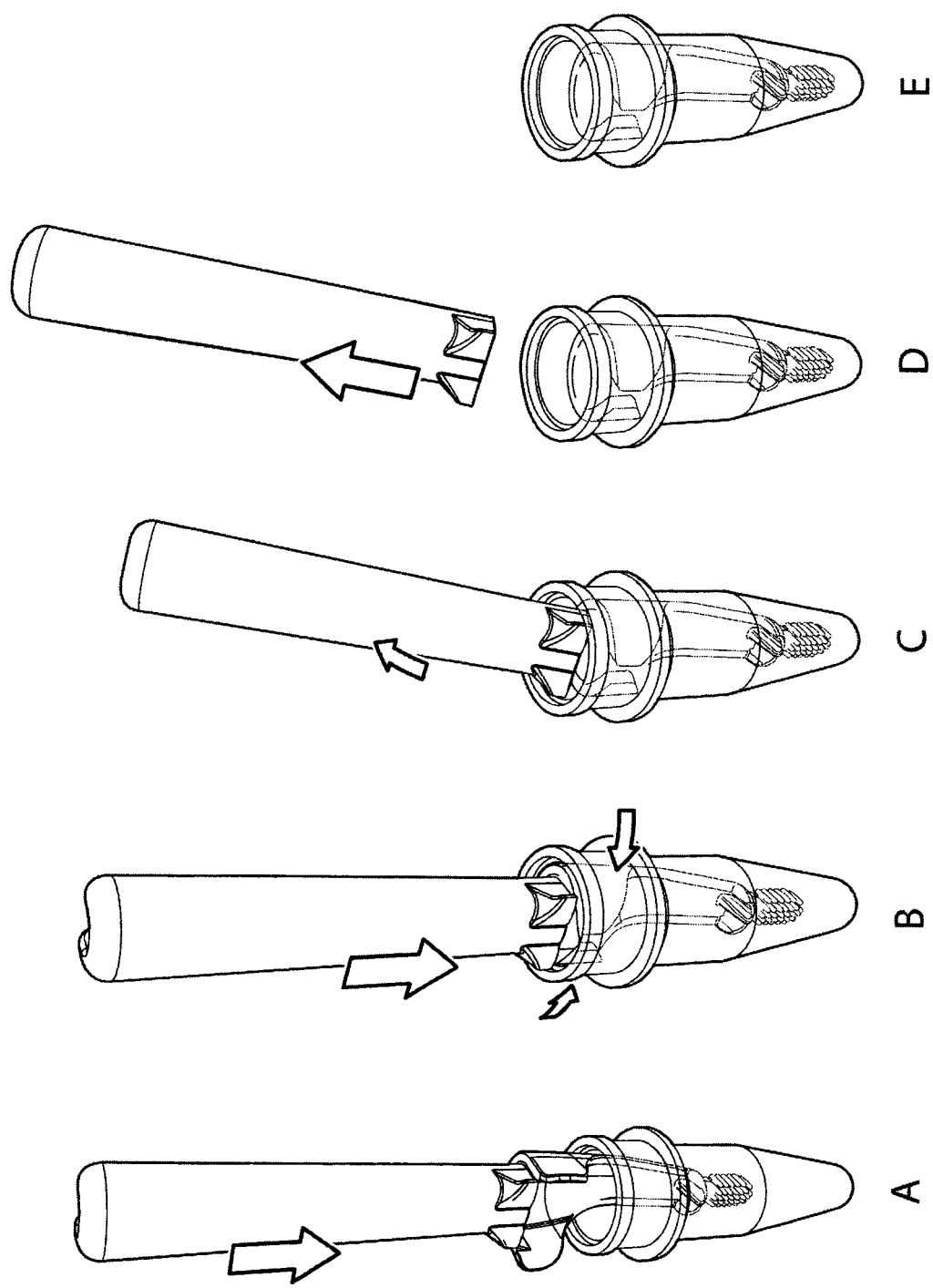
FIG. 11a is illustrating a third step of the method for collecting an oral sample and encapsulating a portion of the sample collecting tool of FIG. 1 containing the oral sample into a PCR or microcentrifuge tube.
FIG. 11b is illustrating a fourth step of the method for collecting an oral sample and encapsulating a portion of the sample collecting tool of FIG. 1 containing the oral sample into a PCR or microcentrifuge tube.
FIG. 11c is illustrating a fifth step of the method for collecting an oral sample and encapsulating a portion of the sample collecting tool of FIG. 1 containing the oral sample into a PCR or microcentrifuge tube.
FIG. 11d is illustrating a sixth step of the method for collecting an oral sample and encapsulating a portion of the sample collecting tool of FIG. 1 containing the oral sample into a PCR or microcentrifuge tube.
FIG. 11e is illustrating a seventh step of the method for collecting an oral sample and encapsulating a portion of the sample collecting tool of FIG. 1 containing the oral sample into a PCR or microcentrifuge tube.

Referring to FIGS. 1 and 2, a sample collection tool 10 for collecting an oral sample from within a mouth of an animal (not shown) without causing significant discomfort to the animal will be described. The sample collection tool 10 comprises a collection end 12 used for collecting an oral sample (e.g., saliva, buccal cells, mucus, sputum, white cells), a first handle portion 14 connected to the collection end 12, and a second handle portion 16 connected to the first handle portion 14 used for manipulation of the sample collection tool 10. A breakable connection 50 between the first handle portion 14 and the second handle portion 16 (described in more detail below), which facilitates separation of the collection end 12 and the first handle portion 14 from the second handle portion 16. The first handle portion 14 and the collection end 12 are dimensioned to fit into a microcentrifuge or PCR tube 30 (such as shown in FIGS. 6-8). The collection end 12 can also be sized and shaped to displace the sample (which is dispersed in the stabilizing solution) to facilitate access and removal of the sample with a sampling pipette. It is contemplated that the sample collection tool 10 could be dimensioned to fit other tubes or other sample receptacles commonly used in the field.

The sample collection tool 10 is a single use tool that allows an operator 4 to safely collect the oral sample and to transfer the sample for storage in the microcentrifuge tube 30 using a single handed motion. In a specific embodiment, the sample collection tool 10 has a total length of about 40 mm. It is contemplated that the length of the sample collection tool 10 could range from about 20 mm to about 25 cm. However, it should be understood that selection of the appropriate dimensions of the sample collection device will depend on its intended application, and will consequently include consideration of not only the subject, but also the source of the sample in the subject (e.g., mouth, vagina, nose, etc.) and also whether the sample is from an animal or a non-animal source (e.g., from a radioactive or biohazardous spill).

The collection end 12, the first handle portion 14 and the second handle portion 16 will now be described in greater detail.

Referring more specifically to FIGS. 3 and 4, the collection end 12 comprises a brush 18 made of a plurality of stubs 20 extending from an ovoid or cylindrical base 22. The stubs 20 are rigid protrusions used to scrape without damaging an inner cheek area of the mouth 2 of the animal in order to collect oral sample therefrom. The stubs 20 have blunt ends for not hurting the animal. As shown in FIGS. 3 and 4, the stubs 20 are arranged in rows which are offset with respect to one another for trapping the oral sample (viscous liquid) between the stubs 20. Although not shown, the stubs 20 can be arranged in other configurations, for example, they can be in alignment with one another rather than offset, or they can be arranged in a purely random manner.

As best seen in FIG. 4, the brush comprises five rows of stubs 20. The number of rows of stubs 20 will depend on various factors, including the size of the ovoid or cylindrical base, the dimensions of the stubs, manufacturing technology etc. Because oral samples are taken from an inner cheeks area of the animal 1, the brush 18 is double-sided. The stubs 20 are parallel to one another and extend vertically from opposite sides of the ovoid base 22 of the brush 18. Oral samples can be taken by scraping the inner surface of the 'left' cheek with one side of brush 18, and then, using the opposite side of the same brush 18, sample can be collected from the 'right' cheek of the animal. However, it is preferable that the stubs 20 extend outwardly around the entire surface of the ovoid base.

In this embodiment, in which the sample being collected is from the mouth of a DOL 1-8 mouse, the collection end 12 is designed to collect about 1-100 microliters of oral sample. Different designs of brush 18 and stubs 20 arrangement would lead to different volumes of collected oral sample. To that effect, the brush 18 and stubs 20 can be designed to adapt to the specific needs of the collection sought by the operator 4. Alternatively, the base 22 could be round, ellipsoid or flat, or even curved. It is contemplated that the stubs 20 could also be arranged in a different manner, and extend angularly from the ovoid base 22, or be positioned on an interface between the two faces of the ovoid base 22. It is also contemplated that brush 18 would have stubs 20 of different heights, or brush 18 has a certain type of stubs 20 on one side of the brush 18 and another type on the other side of the brush 18, or even has the stubs 20 only on one side of the brush 18. Preferably, the stubs 20 are arranged and sized to maximize contact with the inner surface of the animal's cheek.

The collection end 12 is dimensioned to fit inside a cylinder of at least about 2-3 mm in diameter and at least about 2-4 mm in length. Indeed, the collection end 12 is to be inserted into a PCR or microcentrifuge tube 30 of regular size and such as commonly used in the field. Collection end 12 is shaped to fit within the microcentrifuge tube 30 without undue efforts from the operator 4, and to reach a bottom of the microcentrifuge tube 30 tube thereby facilitating immersion of the brush 18 when a limited volume of liquid is introduced into the microcentrifuge tube 30. The liquid is a solution such as, for example, a storage or biomolecule stabilization reagent, a transport solution, an inactivation reagent, or the like.

As seen in FIGS. 1 and 2, the first handle portion 14 has one end 34 connected to the collection end 12 and one end 36 detachably connected to the second handle portion 16. The first handle portion 14 has a substantially conical shape for easing insertion of the sample collection tool 10 into the mouth 2 of the animal 1. The first handle portion 14 is hollow and is dimensioned to be able to receive a pipette 40 in its hollow section 38 (such as seen in FIG. 6). The first handle portion 14 is partially longitudinally cut-away and approximates a scoop shape for easing insertion and operation of the sample collection tool 10 in the mouth 2 of the animal 1. It is contemplated that the first handle portion 14 could have an alternative shape, such as being partially or fully plain, being conical, or being angled in a "V" or "L" shape instead of a scoop shape. However, when designing the first handle portion 14, it is necessary that the end 34 of the first handle portion 14 connected to the collection end 12 must be designed so as to be moved inside the mouth 2 of the animal 1 without causing the animal 1 significant discomfort or injury.

Optionally, the collection tool 10 includes a reagent, such as a biomolecule stabilization reagent, dried or coated on a surface of the first handle portion 14. The location of the dried stabilization reagent on the first handle portion 14, is selected so as to avoid contact of the subject by the stabilization reagent during sample collection and to ensure that it is positioned to be dissolved following addition of the liquid, such as a solution as described above, or water, to the PCR or microcentrifuge tube containing the sample on the collection end 12 and first handle portion 14 of the collection tool. In accordance with one embodiment, the dried reagent is a protease. In accordance with another embodiment, the dried reagent is a combination of ingredients that, when in solution, acts to stabilize biomolecules, including DNA, RNA and/or protein.

In accordance with yet another embodiment, the dried reagent is a combination of ingredients that, when in solution, acts to extract, stabilize, and prepare biomolecules including DNA, RNA and/or protein, facilitating direct analysis of the sample. This reduces hands-on processing steps and enables high-throughput analysis.

Figure 5:
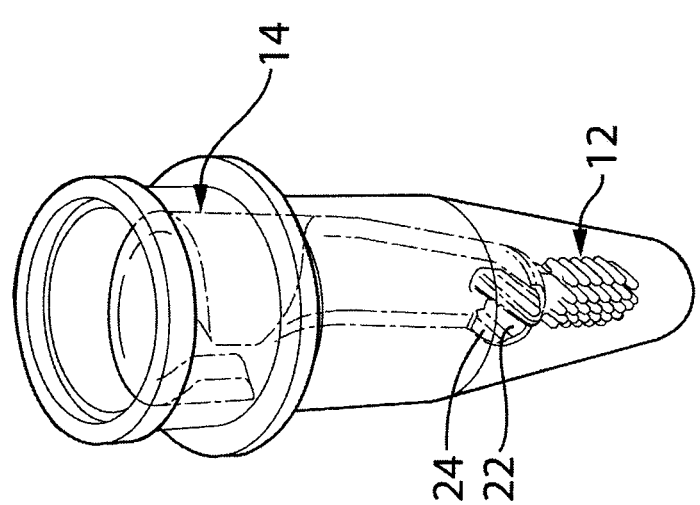
FIG. 5 is a close-up view of a portion of the sample collection tool of FIG. 1 showing a pipette surface.

As best seen in FIGS. 5 and 6, the end of the first handle portion 14 is closed and comprises a pipette receiving surface 22 designed for allowing the pipette 40 that has been inserted inside the first handle portion 14 to rest onto the pipette receiving surface 22, and to prevent the pipette 40 from becoming wedged between the collector end 12 and an inner wall of the microcentrifuge tube 30. In addition, the pipette receiving surface 22 adds displacement volume to move upwards a surface of a solution in the microcentrifuge tube 30. The pipette receiving surface 22 is wide enough to accommodate a tip 42 of the pipette 40. The pipette receiving surface 22 is angled downwardly and comprises ridges 24 for allowing the tip 42 of the pipette 40 to be in fluid communication with fluid contained in the microcentrifuge tube 30. The pipette receiving surface 22 also brings additional support to the connection between the collection end 12 and the first handle portion 14. It is contemplated that the pipette receiving surface 22 could have an annular shape or any other shape that would allow the pipette receiving surface 22 to bring the pipette 20 into fluid communication with surrounding fluid.

Referring back to FIGS. 1 and 2, the first handle portion 14 comprises a pair of winglets 50 located at the end 36 of the first handle portion 14 distal from the collection end 12. Each winglet 50 has some flexibility and is compliant toward a hollow section receiving of the first handle portion 14. The winglets 50 and their compliance are part of a disruption mechanism of the breakable connection 60 that will be explained in greater detail below. Furthermore, the pair of winglets 50 are dimensioned to extend beyond a radius of the microcentrifuge tube 30 when not under stress, and to fit within the radius of the microcentrifuge tube 30 when forced toward the hollow section 38 of the first handle portion 14 (as will be discussed below). The winglets 50 have a rounded shape, but it is contemplated that they could be square or triangular. It is also contemplated that the first handle portion 14 could have only one winglet 50 or could have rows of winglets, such as to define several breakable sections in the first handle portion 14.

The second handle portion 16 has a connection end 44 connected to the first handle portion 14, and another free end 46. The second handle portion 16 has substantially a truncated conical shape. Alternatively the second handle portion 14 could have a cylindrical or square shape. The second handle portion 16 is hollow and is partially longitudinally cut-away. It is contemplated that the second handle portion 16 could have an alternative shape, and be for example plain, as well as having a shape ergonomically suited. For structural purposes during the disruption mechanism as discussed below, a hollow section 48 of the second handle portion 16 faces away from the hollow section 38 of the first handle portion 14. It is contemplated that the hollow sections 38 and 48 of the first handle portion 14 and the second handle portion 16 can face the same direction or be angled with respect to one another.

The connection end 44 of the second handle portion 16 connecting the first handle portion 14 is closed and comprises a reinforcement 54 (as shown in FIGS. 2 and 9) that is generally wedge-shaped. The reinforcement 54 functions to ease the disruption mechanism of the breakable connection 60. Alternatively, the reinforcement 54 can be shaped differently, for example, it can have an annular shape, or can extend through a perimeter of a surface of the connection end 44. The reinforcement 54 can also be omitted and the sample collection tool 10 can be manufactured from a material that is sufficiently stiff or rigid to compensate the omission of the reinforcement 54.

The second handle portion 16 comprises two protrusions 56 located at the end 44. Each of the two protrusions 56 faces a corresponding winglet 50. Each of the protrusions 56 is generally triangular, and a corner of the triangle is in contact with a facing winglet 50 via a breakable attachment. The winglets 50 are each resilient and tend to extend beyond the radius of the microcentrifuge tube 30 for enabling the disruption mechanism. It is contemplated that the protrusions 56 can have alternative shapes such as being in the shape of an arm or being a portion of an annulus.

Referring now more specifically to FIG. 9, the breakable connection 60 will be described. The first handle portion 14 and the second handle portion 16 are connected by the breakable connection 60, which is readily ruptured manually by an operator 4. The breakable connection 60 comprises three breakable attachment points, which physically attach the first handle portion 14 to the second handle portion 16. Once these three breakable attachment points are ruptured, the second handle portion 16 is free from the first handle portion 14 and the collection end 12. The three breakable attachment points are integrally moulded with the sample collection tool 10. First 70 and second 72 breakable attachment points are located at an interface 64 between the pair of winglets 50 and the pair of protrusions 50. A third 74 breakable attachment point is opposite to the winglets 50, and forms with the first 70 and second 72 breakable attachment point an isosceles triangle.

It is also contemplated that the device may only include two breakable attachment points.

It is further contemplated that the third 74 breakable attachment point can have a different position along the end 44 of the second handle portion 16 and that the breakable connection could comprise more than three 74 breakable attachment points. The breakable connection 60 can have the first 70 and second 72 breakable attachment points at the pair of winglets 50, and the third 74 and a fourth breakable attachment points along the end 44 such that the breakable attachment points form a square. It is also contemplated that the breakable attachment points can be distributed all about the interface 72, evenly or unevenly. It is also contemplated that less than three breakable attachment points could be used if for example a single winglet 50 is used in place of the pair of winglets 50. It is also possible to include a breakable attachment band instead of breakable attachment points, as long as the breakable attachment bands are manually and easily ruptured by the operator 4. The size or thickness of each connection point in the breakable connection 60 can be independently adjusted to control the force required to disrupt the connection(s) between the first handle portion 14 and the second handle portion 16.

Referring now to FIGS. 13-17, a sample collection tool 90 advantageously includes an ellipsoid tip 92 at one end of the collection end 94, in which the plurality of raised sampling elements is a plurality of panels extending radially outwardly from all or a portion of the tip 120 in a waffle-type configuration. Each of the panels includes an outward facing edge and lateral side edges coupled to adjacent panels in a waffle-like configuration to form a plurality of indentations extending inwardly from the outward facing edges. The combination of the plurality of panels forms a grid pattern of recesses with an exterior surface formed from the outward facing edges of the panels.

Figure 17:
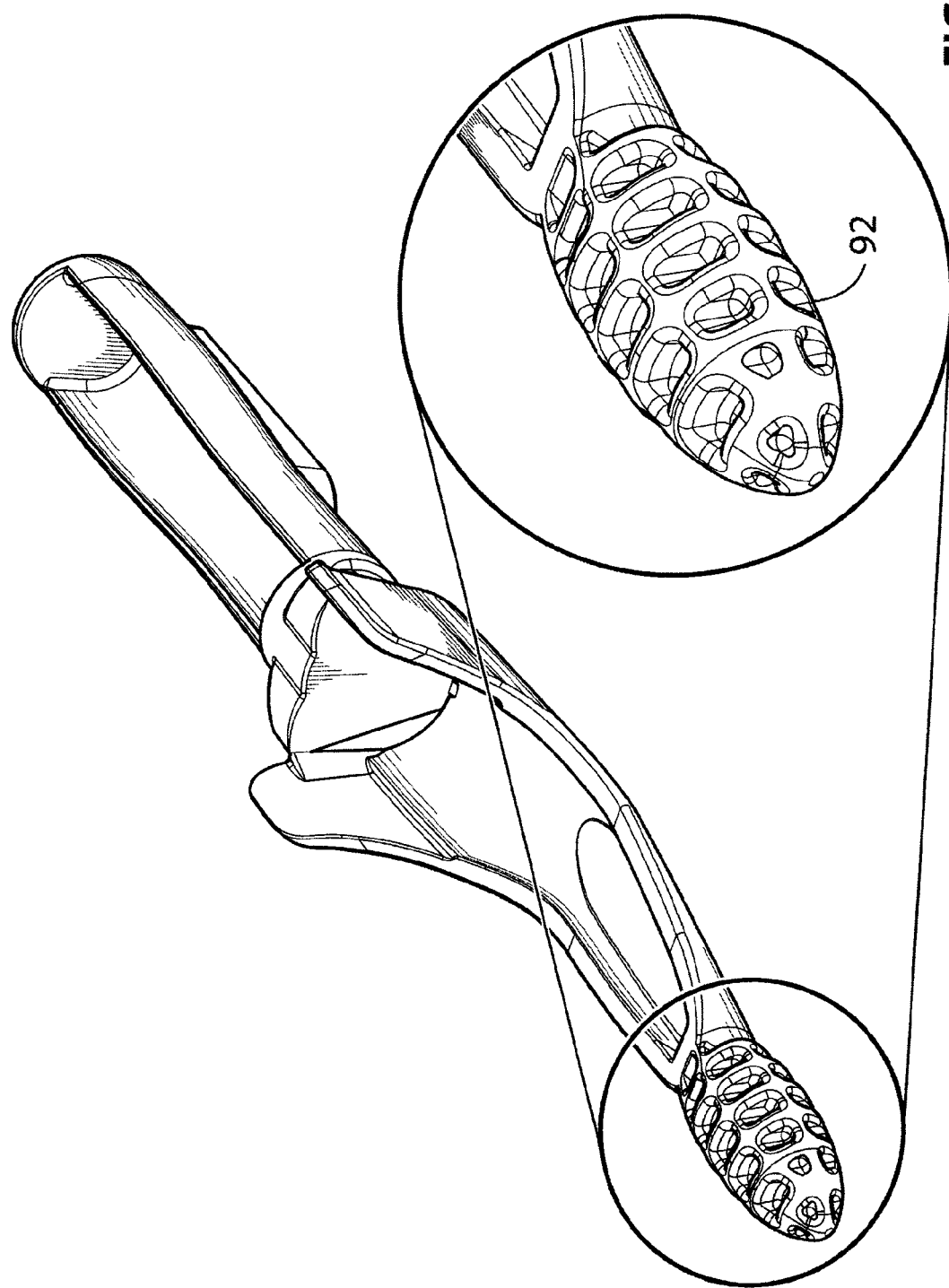
FIG. 17 is a top, left perspective view of the collection tool of claim 13 and a detail of the sample collection tool of FIG. 14.

In one embodiment, as depicted in the detail in FIG. 17, the outward facing edges are bevelled in order to further increase the sample collection surface area. Furthermore, the recesses formed by the plurality of panels can be square, rectangular, oblong, triangular, or another shape, depending on the relative positioning of the panels and on the location of the recess on the ellipsoid collection tip. For example, as shown in the detail in FIG. 17, as the ellipsoid tip tapers 92 toward its free end, the recesses become triangular.

Other embodiments of the sample collection tool are illustrated in FIGS. 24 to 30.

As best shown in FIGS. 24-27, one embodiment of the sample collection tool has a first handle portion 14, a collection end 12 and a second handle portion 16. The second handle portion 16 is designed to allow the user to readily manipulate the tool to a desired orientation for collection of the desired sample. Second handle portion 16 has four sides: a top side 102 (shown more clearly in FIGS. 24 and 26), a hollowed-out bottom side 104 (shown more clearly in FIGS. 25 and 27), and first and second grip sides 106 and 108. Top side 102 indicates to the user which side is "up" for correct initial orientation of the tool. Top side 102 can have any indicators thereon, such as a company name or other marking. It can also be roughened to facilitate gripping of that side of the tool if necessary.

Bottom side 104 is open, exposing a hollowed-out core within the second handle portion 16. A rib 107, integrated with an under surface of the top side 102, extends the length of second handle portion 16 within the hollowed-out core to provide stability to second handle portion 16 and, generally, to the tool. Walls of the hollowed-out core form the inner surfaces of first and second grip sides 106 and 108. A rib surface 112 contains a flat portion for allowing a user to grip bottom side 104 of second handle portion 16. The hollowed-out core permits flexibility to the second handle portion, thus providing favourable ergonomic properties. Further, avoiding the use of unnecessary bulk in second handle portion 16 minimizes malformation of second handle portion 16 during the moulding process.

In use, a user grasps the second handle portion 16. Ideally, the user will immediately and naturally be able to determine the orientation of the tool. If necessary, the user can rotate the tool within their fingers and, based on the feel of the surfaces corresponding to each of the four sides, correctly align the tool for the intended purpose, or position the tool in an orientation which offers more comfort to the user.

The first handle portion 14 of the tool is similar to the connection end 44 of the second handle portion 16 described in other embodiments herein and shown, for example, in FIGS. 2 and 9. The first handle portion 14 can be integrated with the second handle portion 16 in a single moulded handle, yet separated from the second handle portion 16 by a cross guard 114. The cross guard 114 serves as a barrier between the second handle portion 16 and the first handle portion 14, as well as between the second handle portion 16 and the collection end 12. Thus, the cross guard 114 can be useful for reducing the risk of contact between the user's fingers and the sample and, ultimately, reducing the risk of cross-contamination. Further, when inserting the tool into a PCR or microcentrifuge tube with a downward force, the cross guard provides a horizontal surface or stop upon which force can be applied.

Figure 28:
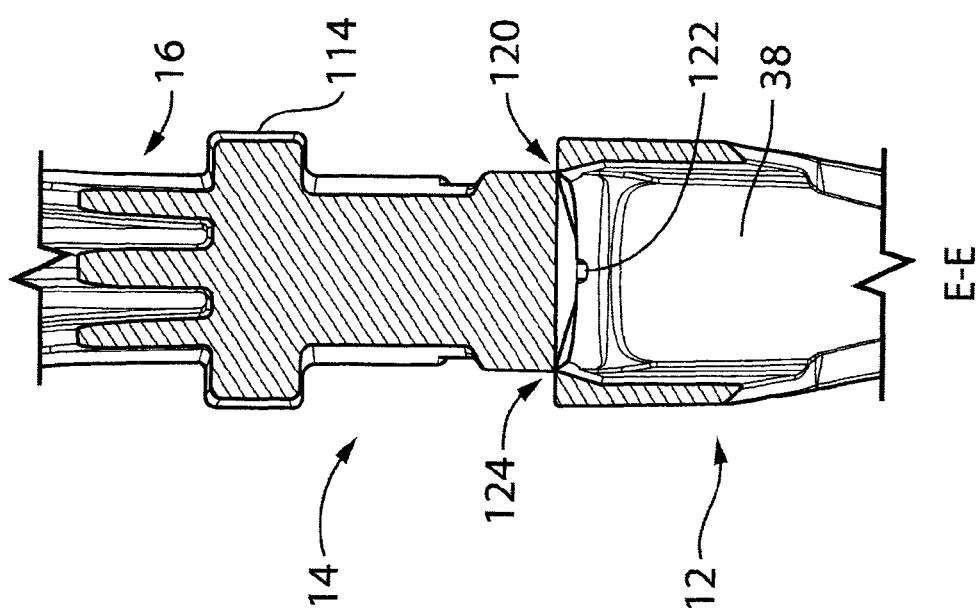
FIG. 28 shows a longitudinal cross section (E-E) of the sample collection tool of FIG. 25.

As best shown in FIG. 28, which is a cross section of the first and second handle portions and collection end, first handle portion 14 is removably attached to collection end 12 by way of three connections at breakable attachment points 120, 122 and 124. The breakable attachment points 120, 122 and 124 are positioned at vertices of a triangle. Breakable attachment points 120 and 124 connect the pair of winglets (shown more clearly as 50a and 50b in FIGS. 24 to 27) to first handle portion 14. In typical use, inserting the collection end 12 into a sample collection tube will force winglets 50a and 50b to bend inward toward the hollow section 38 of the collection end 12, thus causing the breakable attachment points 120 and 124 on the winglets 50a and 50b to break, disengaging the winglets from the first handle portion 14 while still maintaining a connection between the third attachment point 122 and the first handle portion 14. Ideally, the third attachment point 122 has a larger cross section than those of the winglet attachment points 120 and 122, such that the winglets are easier to disengage from the connector portion than the third attachment point. A larger cross section at the third attachment point 122 permits the tip to maintain a point of connection with the connector portion 110, thus preventing premature disengagement of the collection end 12 from the rest of the sample collection tool. The collection end 12 can be completely disconnected from the first handle portion 14 by breaking the connection at the third attachment point 122, as described below under the heading "Sample Collection".

Figure 29:
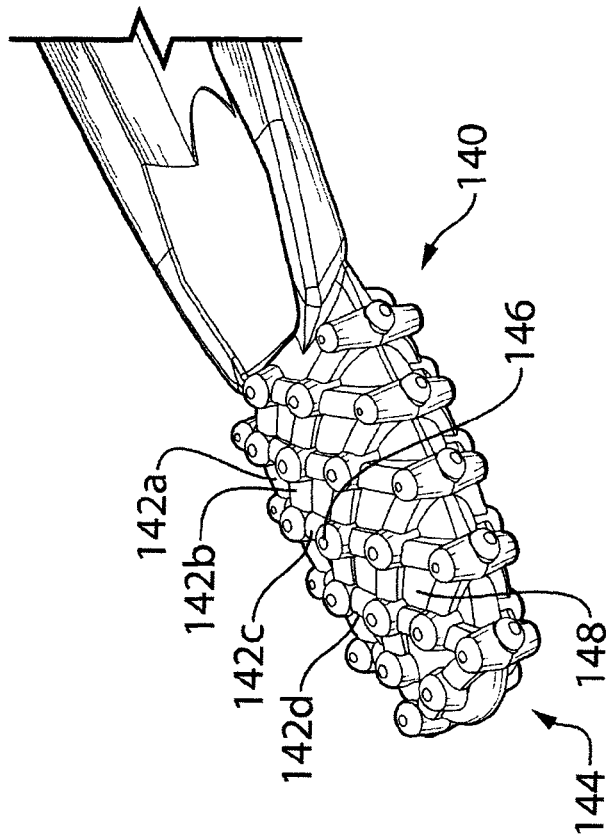
FIG. 29 shows detail of the tip of the first handle portion of the sample collection tool of FIGS. 26 and 27.
Figure 30:
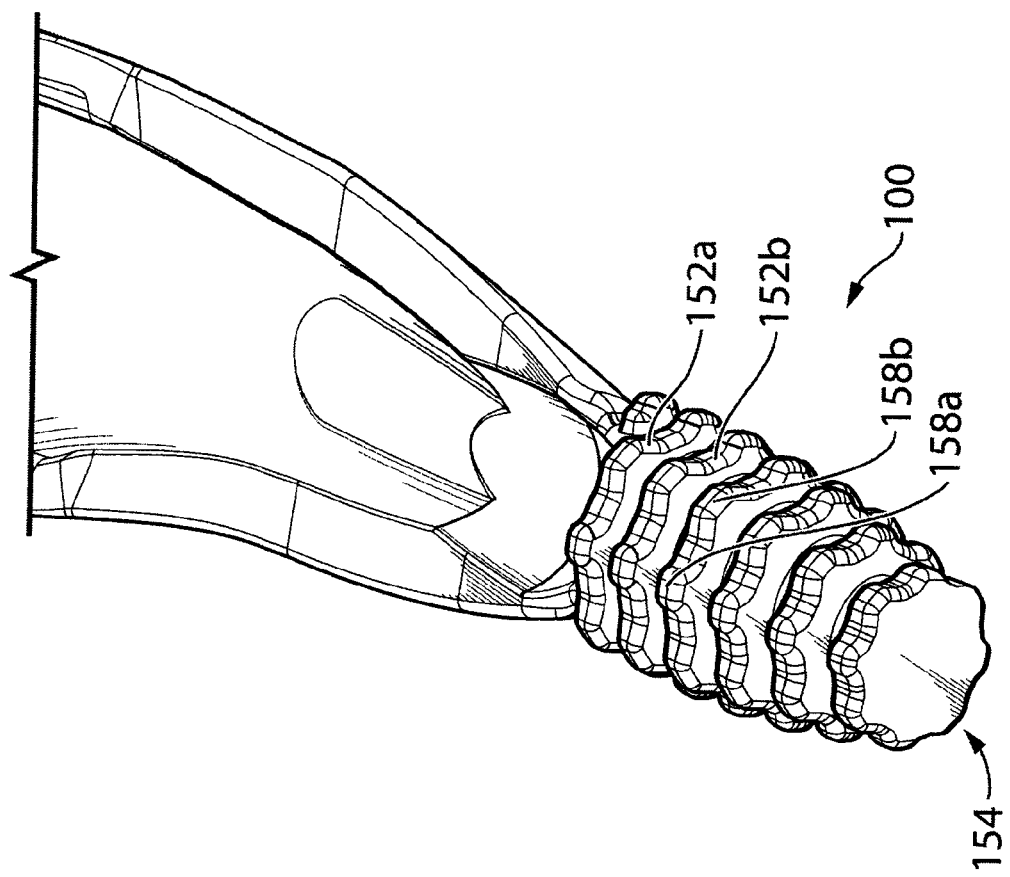
FIG. 30 shows detail of the tip of the first handle portion of the sample collection tool of FIGS. 24 and 25.

Two additional embodiments of the tip at the collection end 12 of the tool are shown in FIGS. 29 and 30. Referring now to FIG. 29, tip 140 has ridges of protuberances projecting generally radially outwardly from all or a portion of the tip in a lattice pattern. Exemplary ridges 142a, 142b, 142c and 142d are identified. The tip 140 is generally ovoid, and "flattened" on two sides to produce two larger faces (i.e., corresponding to the flattened sides) and two smaller faces of the tip. The two larger faces, therefore, have larger surface areas than the smaller surfaces. In a typical orientation of the sample collection tool, the larger faces correspond with the "top" (corresponding to 102) and "bottom" (corresponding to 104) of the second handle portion 16. This permits the user to select a particular orientation of the sample collection tool as desired. With a greater surface area, the larger faces provide more contact with the tissue and, thus, more sample can be collected. For example, if a sample is to be collected from the inside cheek of a rodent, the user will likely select an orientation of the tool such that at least one of the large faces is in contact with the cheek. As will be described herein, the user can readily rotate the tool within one's fingers to adjust the orientation of the tool to permit the desired contact with the sampled tissue.

The larger faces of the tip 140 comprise a lattice pattern of ridges (142a-d) integrated with the tip 140, similar in appearance to the outer surface of a "pineapple" or the like. Within the lattice are generally two sets of parallel ridges, with one set of ridges perpendicular to the other set. As an example, parallel ridges 142a and 142b are perpendicular to parallel ridges 142c and 142d. At the free end 144 and on the smaller faces of the tip 140, the lattice pattern is interrupted. At points where the ridges intersect, stubs (such as 146) integrated within the ridges protrude outwardly from the intersection of the ridges. The stubs 146 can be of any suitable length or shape, but as described elsewhere herein, are sufficiently rigid to scrape the tissue (such as the inner cheek area of the mouth of the animal from which the sample is taken), without damaging the tissue or causing unnecessary pain to the animal. Any number of additional stubs not forming part of the general lattice pattern, such as those shown at the free end 144 of the tip 140, can be present as desired.

Within the lattice structure, cavities (such as 148) are formed between two pairs of perpendicular ridges. Ideally, the cavities 148 are of a sufficient depth such that adequate amounts of sample can be "trapped" within the cavities 148 to improve the yield of sample obtained from the animal, yet sufficiently shallow such that the sample can readily be removed therefrom for analysis.

Referring now to FIG. 30, a further tip embodiment 100 is shown. In this embodiment, a tapering, or conical, tip having a generally circular cross sectional area is provided. The circular cross section is particularly advantageous for ensuring a consistent orientation during sample extraction, and may also be more practical for less experienced users or those with limited manual dexterity, as the orientation of the handle in one's fingers is not as critical as it is with other embodiments of the present tool.

Parallel rings of raised ridges (such as 152a and 152b) encircle the tip 100. The rings are progressively smaller in circumference as the tip 100 tapers towards the free end 154, generally forming a "honeydipper" appearance or the like. The ridges 152a and 152b generally extend radially outwardly from the tip and can be of any suitable height. In one particular embodiment, one or more rings of ridges have a plurality of stubs (such as 158a and 158b) extending outwardly therefrom, thus forming a series of convoluted rings around the tip. With the stubs 158a and 158b, additional surface area is provided on the tip 100 to increase yield of sample obtained. However, it is also contemplated that the ridge height may be made uniform around the circumference of the tip, without any stubs present, should a less convoluted surface area be desired.

Sample Collection

Referring to FIG. 36 (panels 6a to 12), a sample collection method using the collection tool as described herein is provided.

In an exemplary use, an operator grips the sample collection tool by the second handle portion (panel 7) and inserts the collection end inside the mouth of an animal with one hand (panel 8), while holding/restraining the animal with the other hand (panels 6a, 6b). The operator then uses the collection end to scrape or rub a surface of the inner cheeks of the animal using a back and forth, up and down, or rolling motion against the inner cheeks of the animal (panel 9). Sufficient pressure should be applied to the inner cheeks to ensure that the tool is in adequate contact with the surface. Typically, the operator will be able to gauge the pressure applied by the tool to the inner cheek by placing the thumb and/or forefinger of the restraining hand over the outer surface of the cheek pouch. Once sufficient oral sample has been collected from both cheeks, the operator removes the sample collection tool from the mouth of the animal and inserts the collection end of sample collection tool into a clean PCR or microcentrifuge tube (panel 10). As the pair of winglets start to abut the tube, the operator continues to insert the sample collection tool by slightly forcing it into the microcentrifuge tube. The pair of winglets are resilient and are forced to move toward the hollow section of the first handle portion as the collection tool is placed in the microcentrifuge tube. During this step, the first and second breakable attachment points break. At this point, the first handle portion is inside the microcentrifuge tube, and is linked to the second handle portion by only the third breakable attachment point. The operator applies downward force and/or twists or bends the second handle portion in order to rupture the third breakable attachment point (panel 11). Preferably, the operator applies a downward force and then pushes or bends the second handle portion away from them at approximately a 45° angle. In certain embodiments of the tool, indicators such as arrows or the like may be added to the free end of the second handle portion to provide the user with directions for moving or bending the second handle portion to produce an effective break of the third breakable attachment point. FIGS. 11a to 11e show another embodiment of the insertion of the collection end of the tool into a tube, and the rupturing of the collection end from the first and second handle portions. The second handle portion is then discarded and the PCR or microcentrifuge tube can be sealed again with any suitable cap while containing the first handle portion and the collection end with the oral sample (FIG. 36, panel 12). In one embodiment (not shown), one end of either the first or second handle portion of the tool has a cap thereon. The cap can be integrally moulded within the handle portion(s). This "built-in" cap on-board the collection tool can be used for capping and/or sealing the collection tube. In any case, the sample collection tool described herein is ideally intended for single use only. This reduces the likelihood of cross-contamination between samples.

In situations in which the collection tool is used for sample collection in other cavities, the sample collection end is inserted into the cavity and moved within the cavity in much the same manner as currently used collection tools, such as swabs and brushes. Ideally, the tool can be sized and shaped for use in the desired sample collection cavity. The size and shape should be chosen such that the collection end can adequately contact the wall(s) of the cavity to be sampled, and can obtain a sufficient quantity of the sample to be analyzed. The size and shape should also be chosen to facilitate use by the operator. Following sample collection, the collection tool is withdrawn from the body cavity and the collection end is placed in a sample receiving receptacle as described above. Optionally, the collection tool is used together with a speculum to improve access to the target sampling area within the body cavity, or other sample collection area. However, it will be appreciated that even trace amounts of sample can be collected with the collection tool described herein, and that the trace amounts can be captured on the collection tip and retained within the collection receptacle for further analysis. This is particularly advantageous when compared to other means of sample collection which do not offer the same level of confidence. For example, it can be difficult to determine whether a sample of tail snip is present in a collection tube. Further, hydrostatic forces, surface tension and evaporation can contribute to hampering the ability of collecting and retaining a sample in a microcentrifuge tube for performing PCR In accordance with another aspect, there is provided a sample collection kit, the kit comprising one or more of the sample collection tools as described herein and one or more collection receptacles. The sample collection tools can be provided loose or in links of two or more tools connected to a strip (FIG. 12), typically of the same material as the tools, from which individual tools are broken off prior to use. Strips of collection tubes can similarly be provided in the kit.

Figure 32:
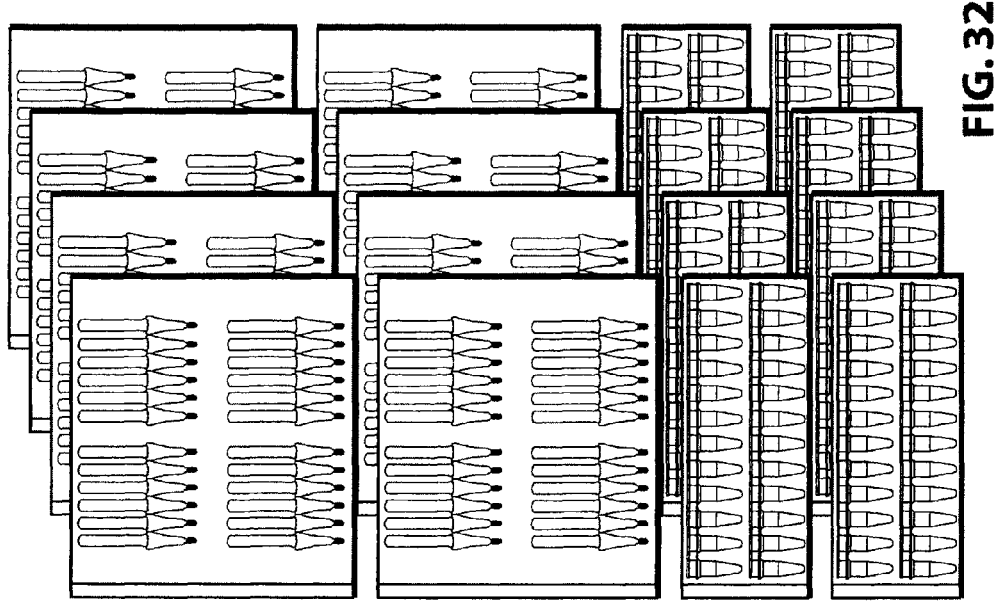
FIG. 32 depicts another embodiment of the kit comprising sample collection tips and tubes.
Figure 31:
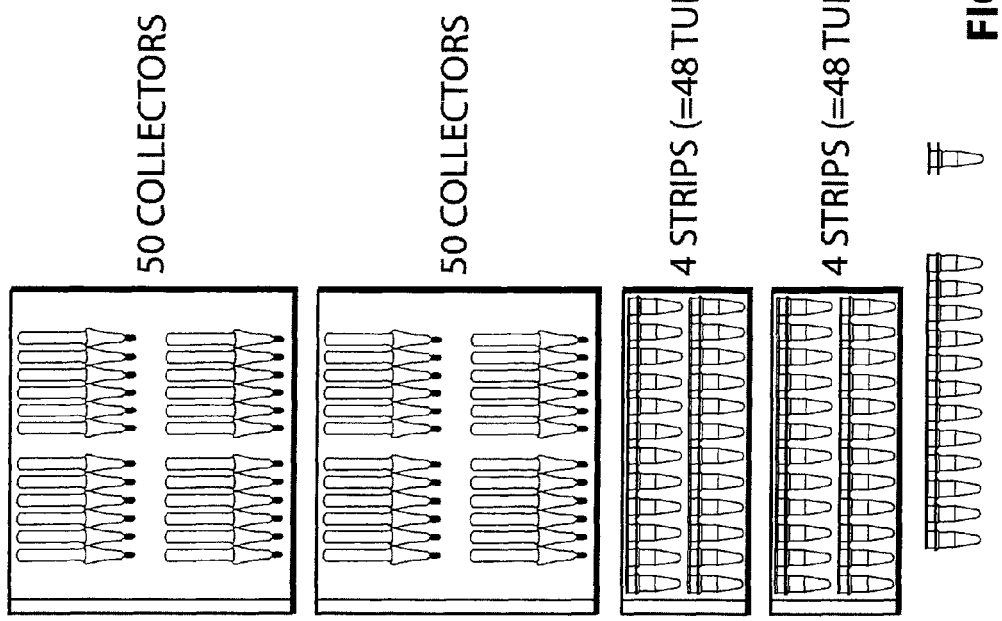
FIG. 31 depicts one embodiment of the kit comprising sample collection tips and tubes.

In one exemplary embodiment shown more particularly in FIG. 31, the kit contains up to 100 sample collection tools and 96 collection tubes. Optionally, the tubes can contain a liquid stabilizing reagent (as described herein), such as a nucleic-acid stabilizing or preserving reagent, or some other fluid as desired, depending on the end use of the collected sample. A further embodiment of the kit is shown in FIG. 32, whereby a plurality linked tools and tubes are provided for higher throughput applications.

The collection tubes can be any desired size with any suitable closing mechanism, such as flip cap, push cap or screw top. The dimensions of the tube are generally selected to be appropriate for particular downstream applications, such as amplification—(e.g. PCR) and hybridization-based assays. In some embodiments, standard laboratory 100, 200, 500, 1000, 1500 or 2000 µL microcentrifuge tubes may be more particularly suitable. In addition, the amount of stabilizing or other reagent present (if desired) should be kept to a minimum to maintain an appropriate concentration of the sample, thus reducing any unnecessary post-collection preparation steps.

Once the first handle portion is placed into the collection tube and has been severed from the remaining handle portions, the collection tube can be closed, sealing the tip, collected sample and buffer (if present). The sample can then be analyzed as required. Optionally, the lid used to close the collection tube is a pierceable lid, such as those suitable for use in automated testing or by liquid-handling robots.

It is desirable for sufficient fluid to be present in the collection tube (i.e., sample plus any added buffer or other liquid) such that it is displaced above the top of the tip. Ideally, larger debris which may have been extracted from the animal during sample collection, will settle to the bottom of the collection tube and out of reach of a pipette. It may be necessary for a user to gently flick the bottom of the tube to loosen any debris from the tip, thus allowing more fluid to be available above the tip or above a pipette receiving surface (as described above) if present. If there is sufficient fluid (ideally, 10-20 µL for most sample analyses) displaced in the tube above the tip, the fluid can be readily extracted from the tube without the need to first remove the tip. The fluid above the tip can be extracted using a standard pipette tip which, preferably, fits within a channel formed by the resilient opposing winglets of the first handle portion which, after insertion into the collection tube, forcedly abut the interior surface of the tube.

In an alternative embodiment, the sample collection receptacle is a well or cuvette within a multiwell or multicuvette plate, array or strip. In this example, the first handle portion is placed within a well or cuvette in the same manner as described above for use with a collection tube such, that the winglets forcedly abut the inner surface of the well or cuvette and such that the first handle portion can be severed from the rest of the tool to facilitate downstream sample analysis. As with the collection tubes, it is desirable for sufficient fluid to be present in the collection well or cuvette (i.e., sample plus any added buffer or other liquid) such that the fluid is displaced above the top of the tip. If there is sufficient fluid (ideally, 10-20 µL for most sample analyses) displaced in the tube above the tip, the fluid can be readily extracted from the tube without the need to first remove the tip. The fluid above the tip can be extracted using a standard pipette tip which, preferably, fits within a channel formed by the resilient opposing winglets of the first handle portion. This embodiment is particularly well suited to applications in which robotic testing is performed following collection. Optionally, the kit includes covers or lids for the multiwell or multicuvette plates or strips or arrays.

Sample Collection Tool Manufacturing

Figure 12:
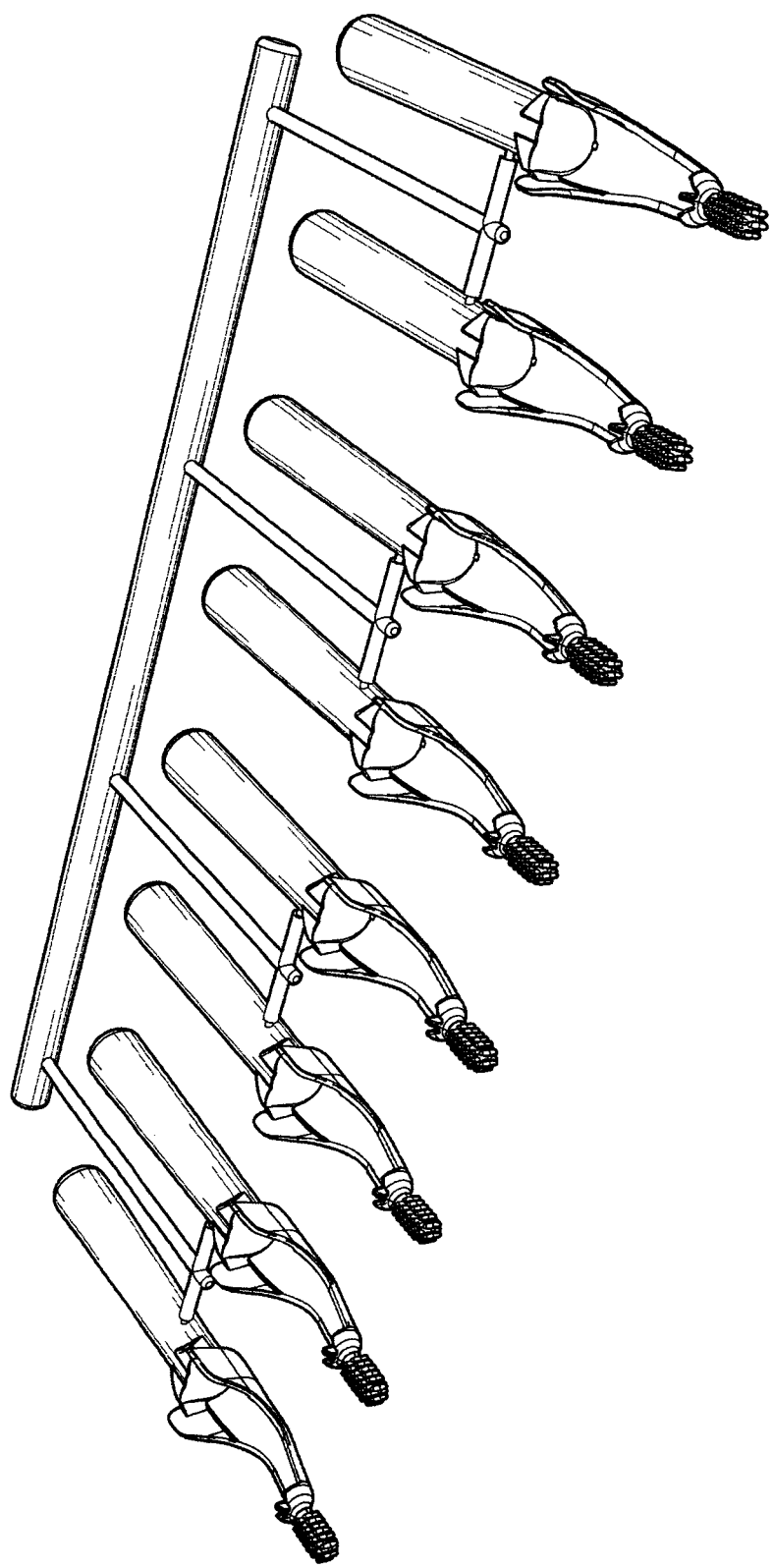
FIG. 12 is a perspective view of a plurality of the sample collecting tools of FIG. 1 produced from a multiple cavity injection mould.
Figure 13:
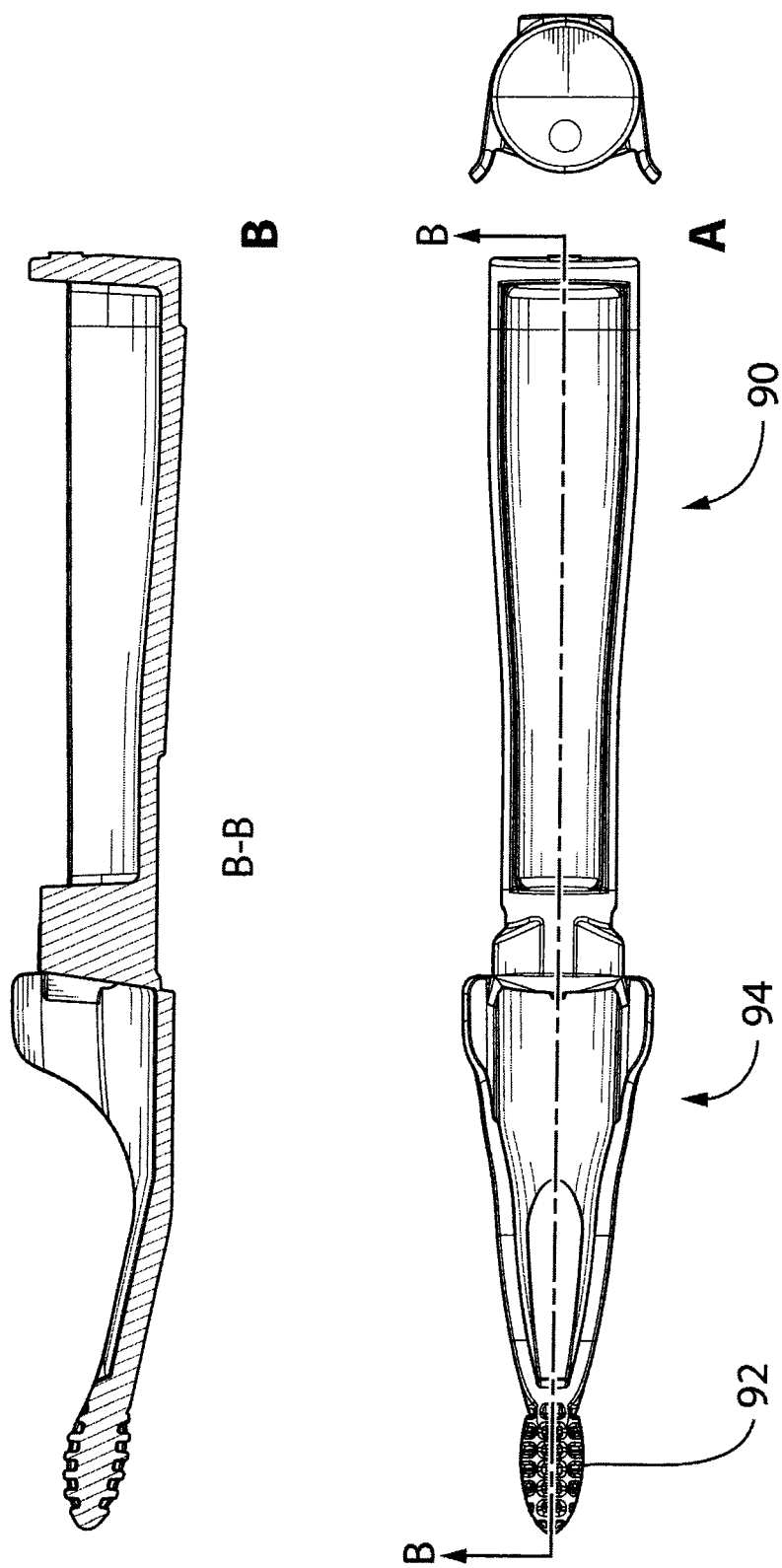
FIG. 13 is (A) a front view of a sample collection tool according to one embodiment, and (B) a cross-sectional view of the collection tool depicted in FIG. 13A.
Figure 14:
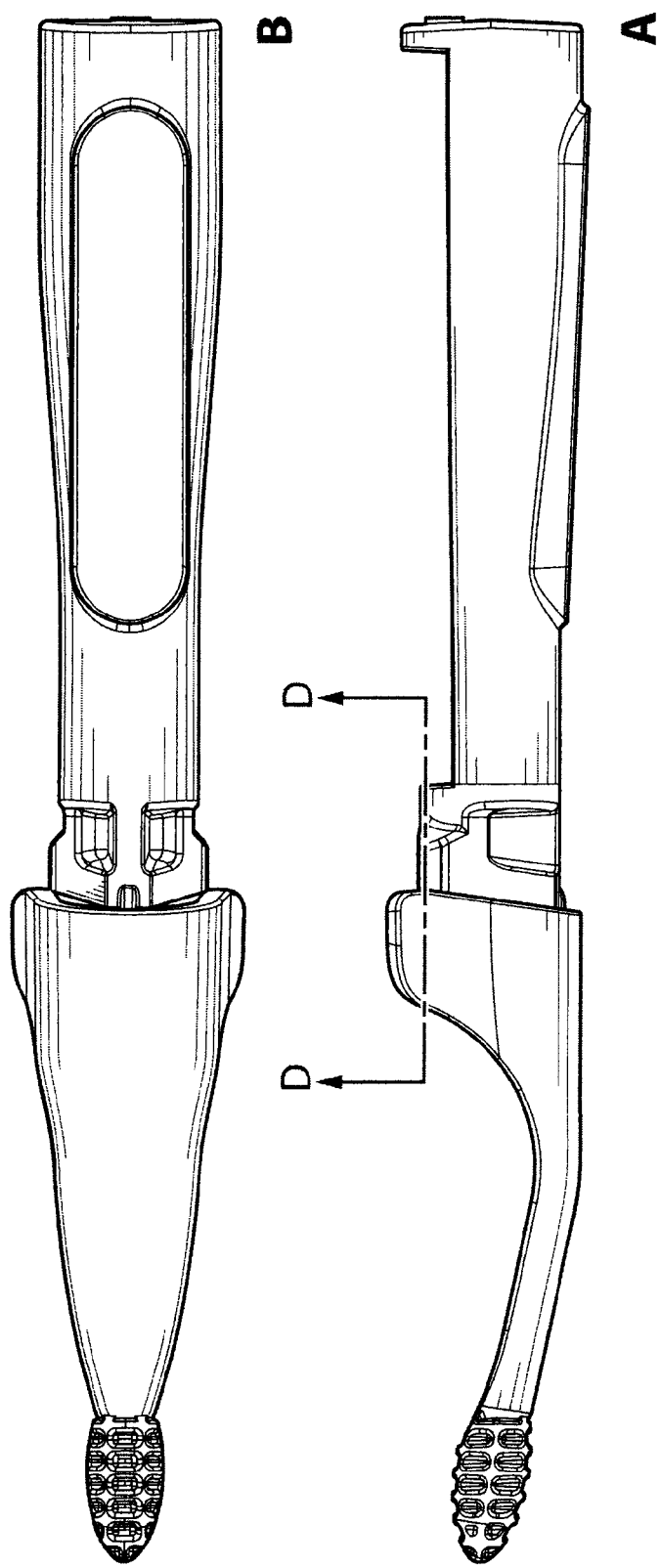
FIG. 14 is a side view (A) and a back view (B) of the collection tool of FIG. 13.
Figure 15:
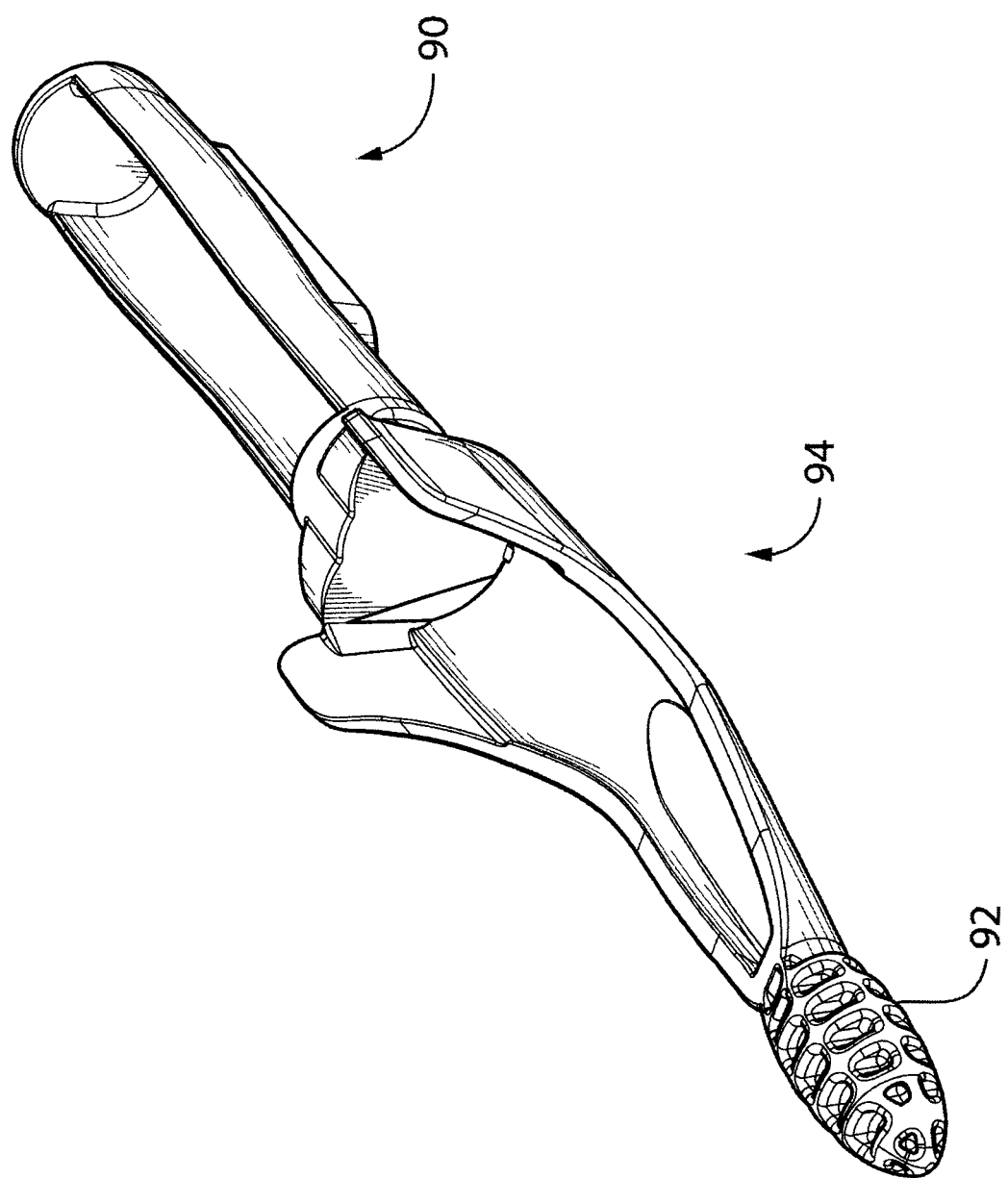
FIG. 15 is a side, perspective view of the collection tool of FIG. 13.
Figure 16:
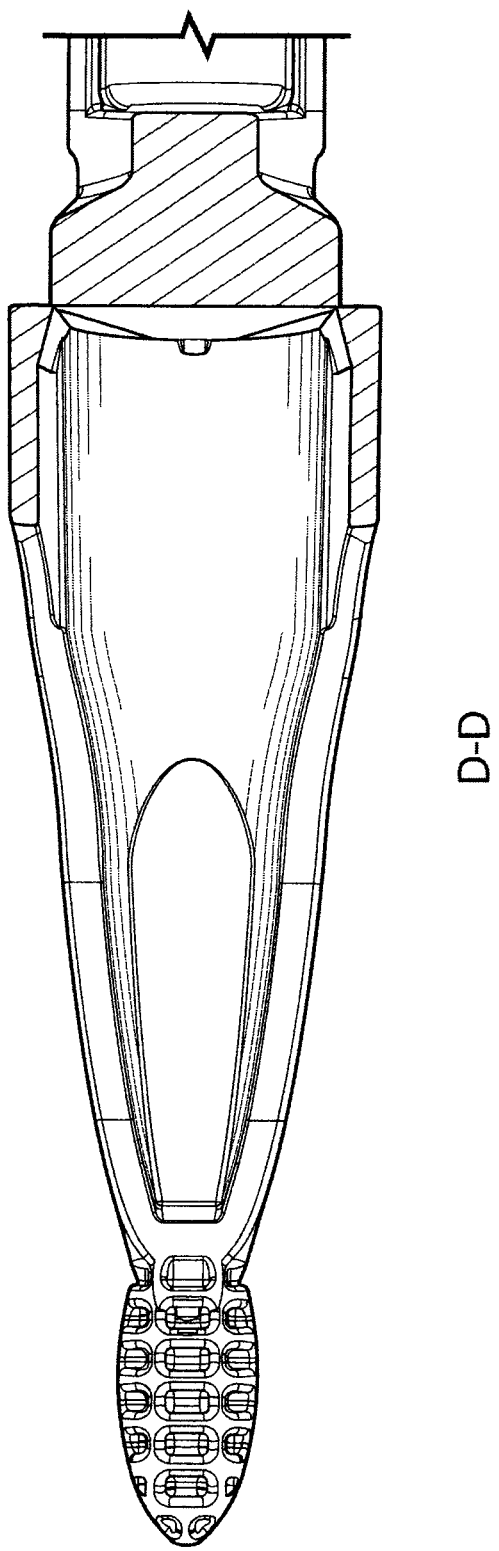
FIG. 16 is a cross-sectional view along line D-D of the collection tool of FIG. 14A.

Referring now to FIG. 12, the collection tools described herein are preferably manufactured from a thermoplastic or combination of thermoplastics using standard injection moulding or micro-moulding. As shown in FIG. 12, a series of collection tools can be manufactured together using a single, multiple impression/cavity or injection mould.

Standard injection moulding, micro-injection moulding, and casting processes can be used to manufacture the collection tool. In addition, electrical discharge machining (EDM) and laser cutting can be used in the manufacture of the collection tool. In the case of high volume production runs, high speed methods can be employed.

Suitable plastics useful for manufacturing the collection tools include, but are not limited to: polypropylene, high-flow polypropylene, mineral-filled polypropylene, polystyrene, high-impact polystyrene, polyethylene, medium-density polyethylene (MDPE), high-density polyethylene (HDPE), polyvinyl chloride (PVC), and polycarbonate.

To gain a better understanding of the invention described herein, the following examples are set forth. It should be understood that these examples are for illustrative purposes only. Therefore, they should not limit the scope of this invention in any way.

EXAMPLES

Example 1

Total DNA yield was determined from the use of a collection tool that does not include raised sampling elements and compared to the total DNA yield obtained using a collection tool according to the present invention that does include raised sampling elements. In this case, both collection tools include a collection tip that is approximately ovoid and has a concave face so as to form a scoop-like collector. The collection tool of the present invention additionally included raised sampling elements on the convex face of the scoop-like collector.

Figure 18:
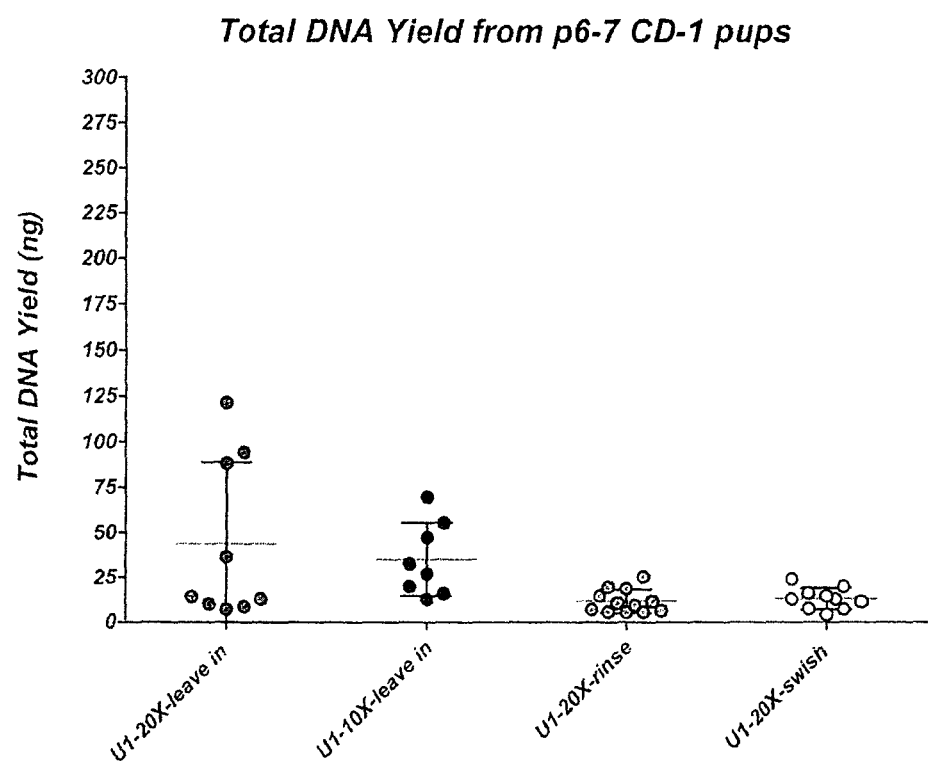
FIG. 18 graphically depicts DNA yield obtained using a prior art sample collection device.

In the first study, oral DNA collection was performed on p6-7 CD-1 mouse pups using the collection tool having a scoop-shaped collection end ("U1", see Zhang et al., supra), without any raised sampling elements. Each device was gently scraped ten times on the inside of one cheek (10×) or on the inside of two cheeks, consecutively (20×). The device was then left in the stabilizing solution for processing (leave in), rinsed several times in the stabilizing solution by pipetting up and down (rinse), or "swished" several times in the stabilizing solution (swish). Each device was placed in a single microcentrifuge tube containing 200 µL stabilizing solution; for both rinse and swish experiments, the devices were then discarded prior to processing. Total DNA was isolated from each tube, resuspended in 50 µL TE and quantified. The results are provided in the graph of FIG. 18. Collecting either 10× or 20× resulted in comparable amounts of total DNA (compare column 1 to column 2). The rinse and swish collections methods resulted in reduced DNA yield (compare column 1 to columns 3 and 4). All four methods (column 1-4) using U1 devices collected very little DNA (<25 ng) in most cases.

Figure 19:
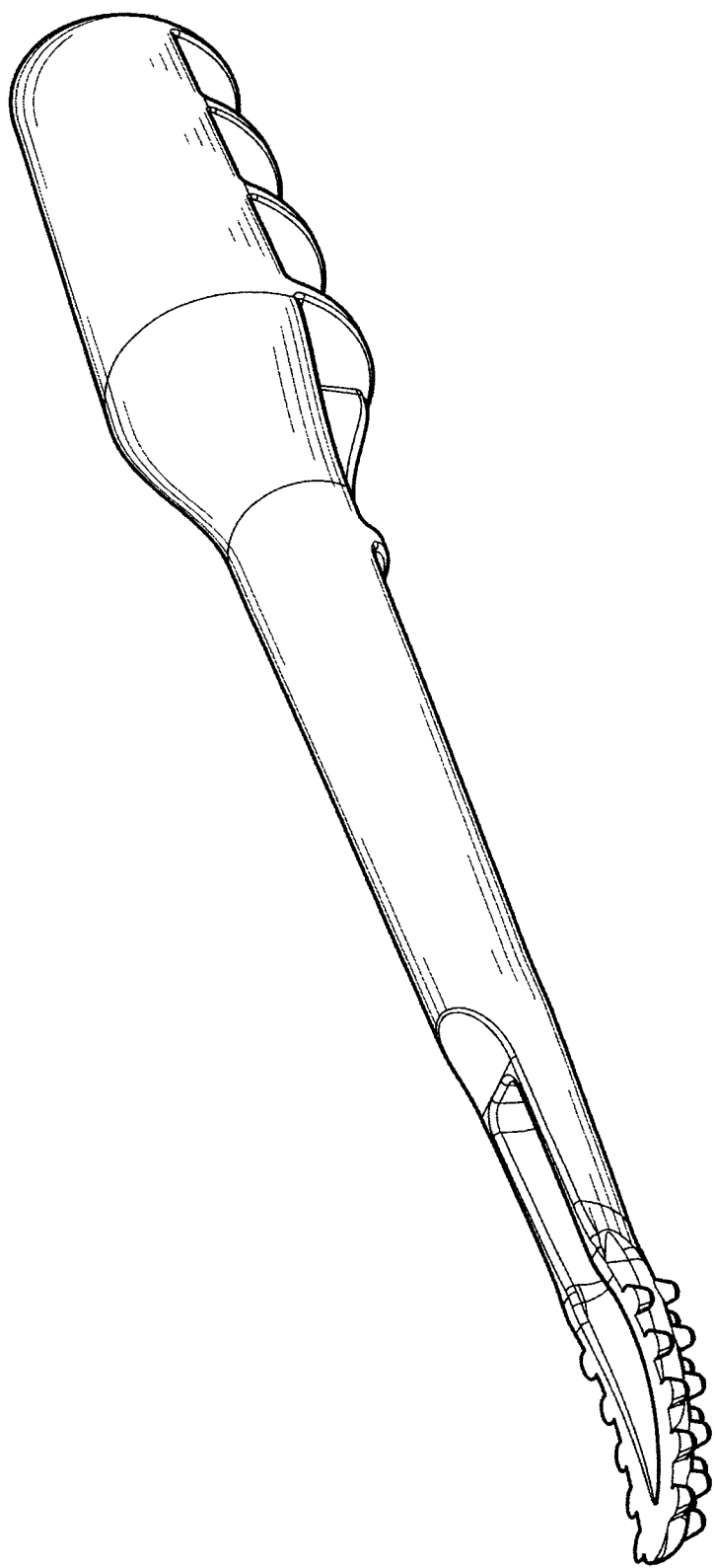
FIG. 19 is a side, perspective view of a collection tool according to one embodiment, which includes a plurality of raised bumps.
Figure 20:
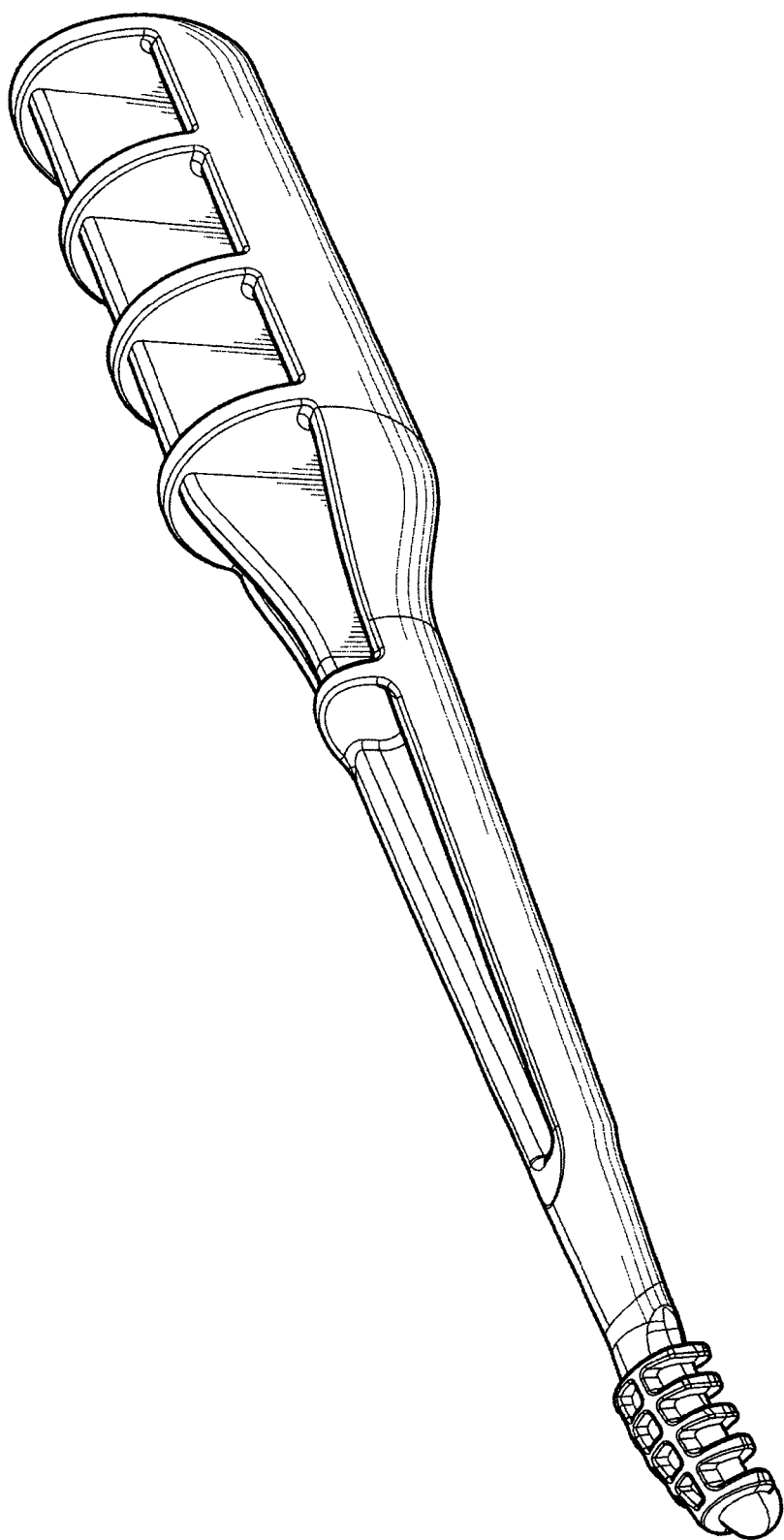
FIG. 20 is a side, perspective view of a collection tool according to one embodiment, which includes a plurality of raised ridges.
Figure 21:
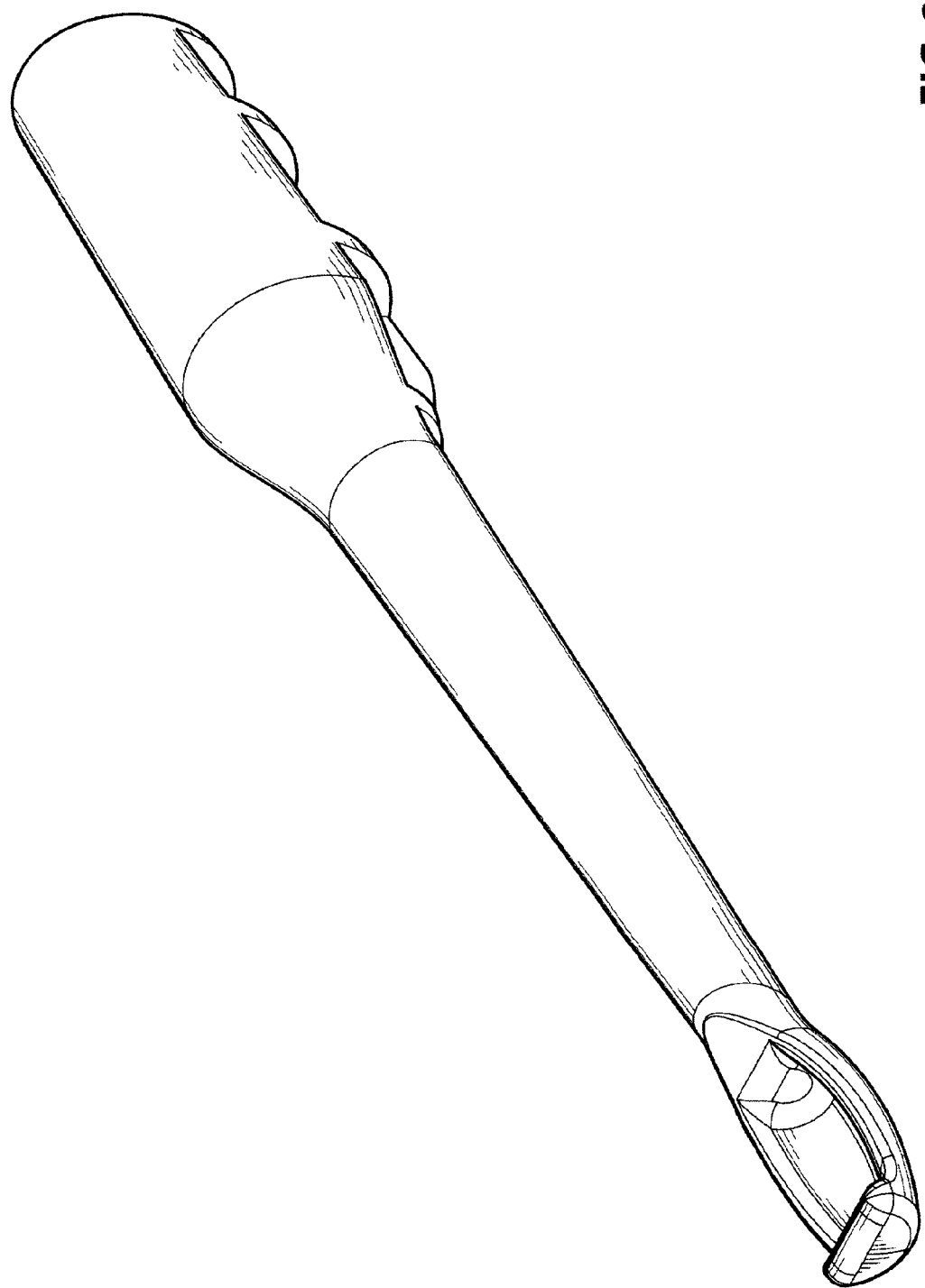
FIG. 21 is a side, perspective view of a collection tool including a hooked tip.

Oral DNA collection was performed on p6-7 CD-1 mouse pups using five types of collection tools having different collection ends: (1) a scoop-shaped collection end ("U1"); (2) a moulded, scoop-shaped collection end similar to U1 ("US"); (3) a moulded, scoop-shaped collection end having a plurality of raised bumps on the convex surface of the scoop ("UB"; FIG. 19); (4) a moulded, scoop-shaped collection end having a plurality of raised ridges on the convex surface of the scoop ("UR"; FIG. 20); and (5) a moulded, scoop-shaped collection end having an added a hook element at the tip of the scoop ("UH"; FIG. 21).

Figure 22:
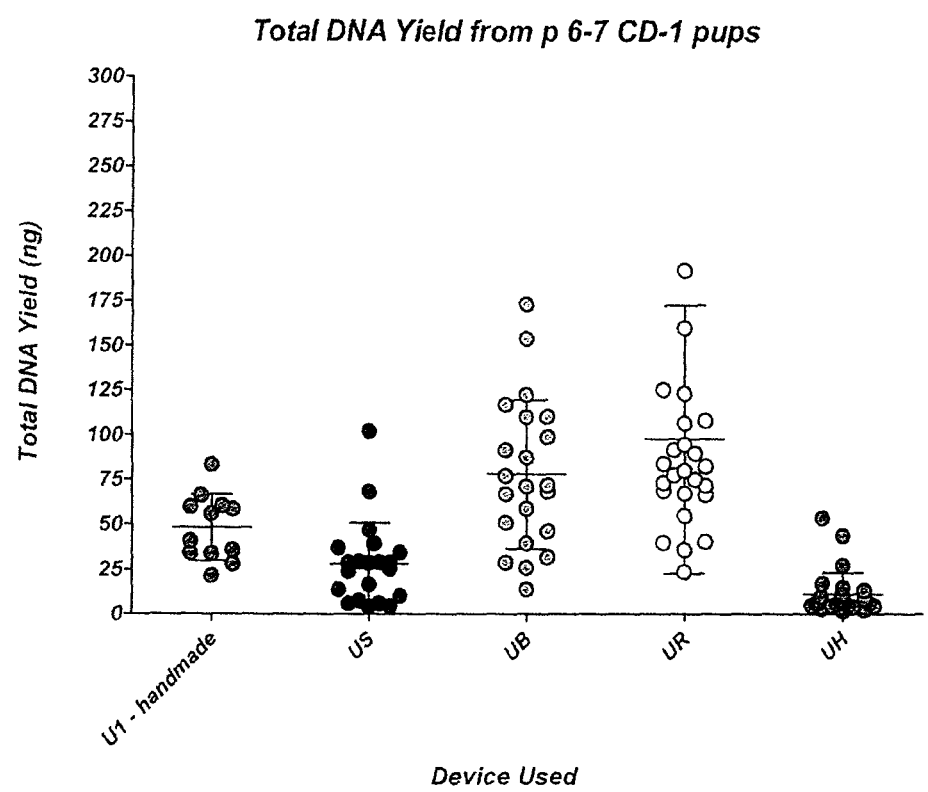
FIG. 22 graphically depicts DNA yield obtained using a prior art sample collection device in comparison to sample collection devices according to specific embodiments.

Each collection tool was gently scraped ten times on the inside of two cheeks, consecutively (20×). The collection tool was then left in the stabilizing solution for processing. Each collection tool was placed in a single microcentrifuge tube containing 200 µL stabilizing solution. Total DNA was isolated from each tube, resuspended in 50 µL TE and quantified. The data are presented in FIG. 22 as a vertical scatter plot with mean (line)+/− standard deviation. Collecting with the UB and UR prototypes resulted in the highest DNA yields (compare columns 1 and 2 to columns 3 and 4).

Example 2

Oral DNA collection was performed on p8-9 CD-1 mouse pups using a collection tool of the present invention that includes a moulded, scoop-shaped collection end having a plurality of raised ridges on the convex surface of the scoop ("UR"; FIG. 20).

Figure 23:
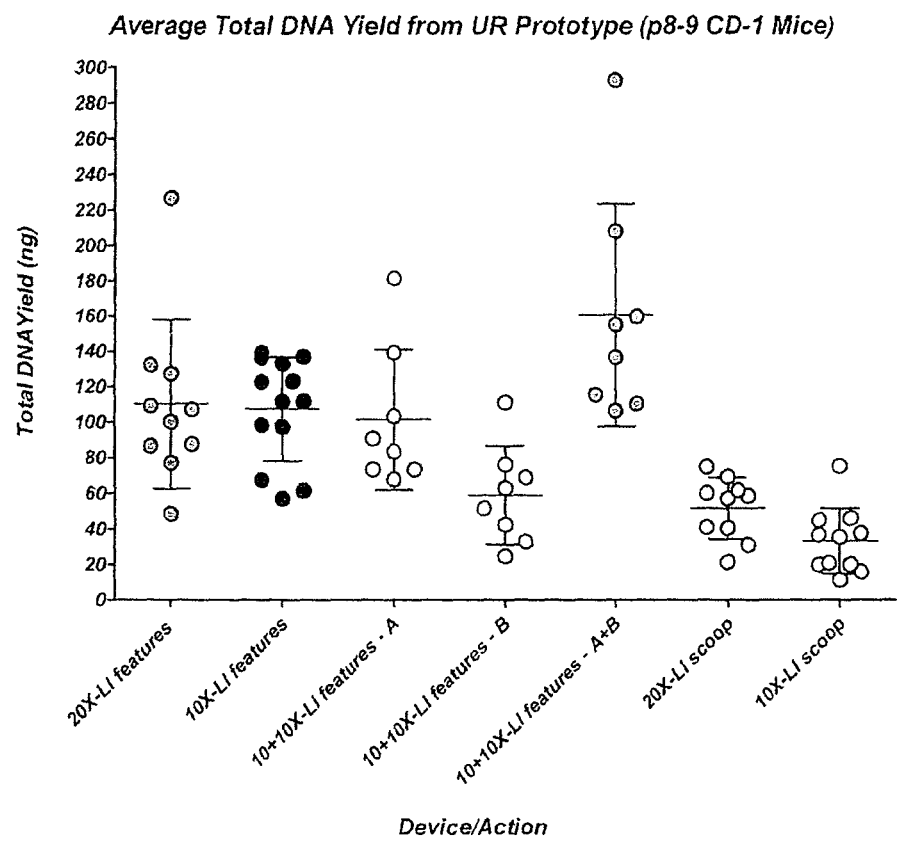
FIG. 23 graphically depicts DNA yield obtained using a prior art sample collection device in comparison to sample collection devices according to specific embodiments.
Figure 24:
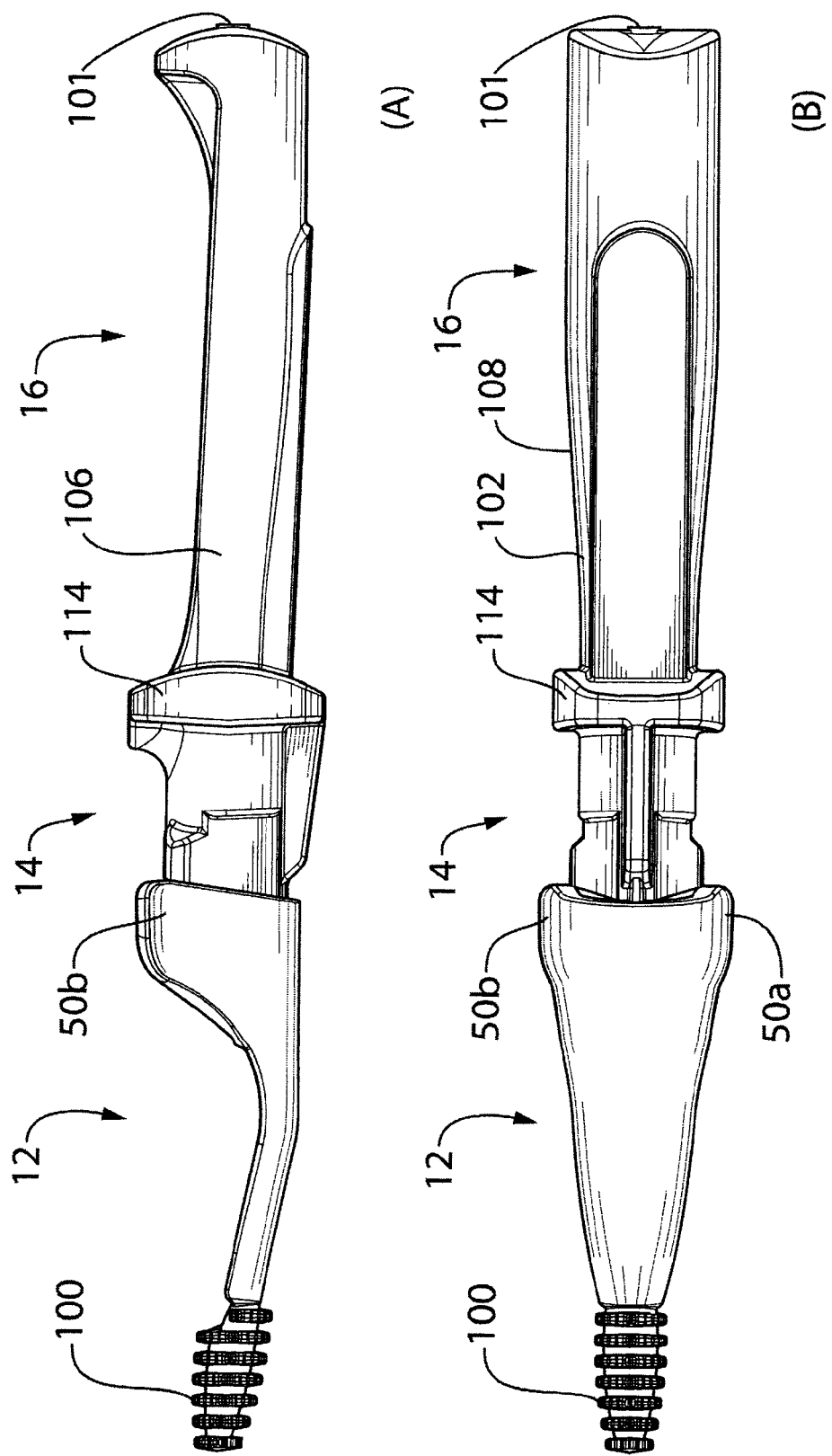
FIG. 24 is a side view (A) and top view (B) of a sample collection device according to one embodiment.
Figure 25:
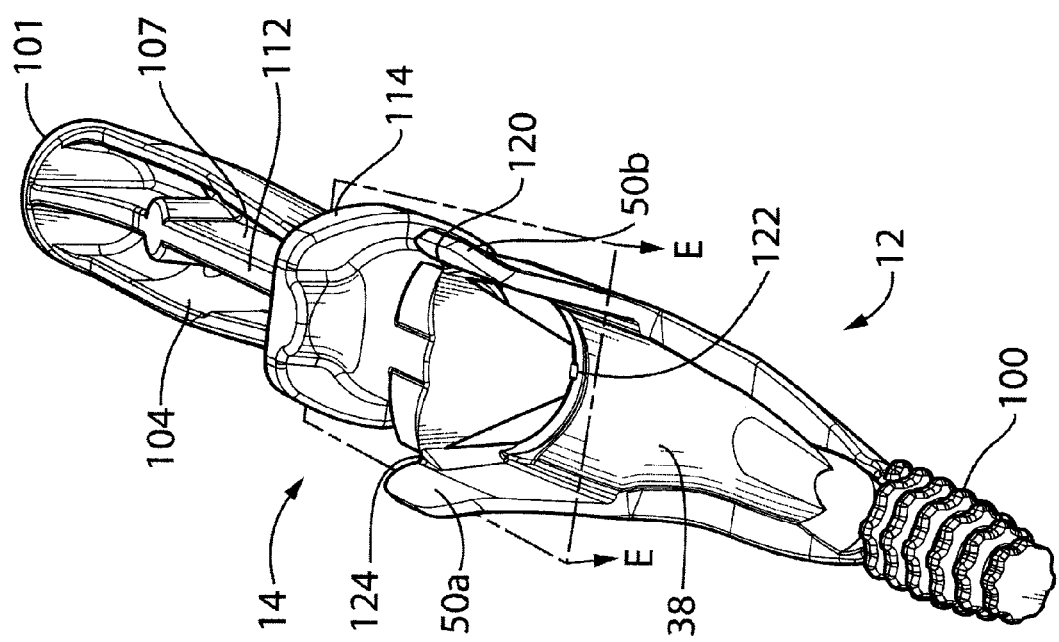
FIG. 25 shows a bottom view of the sample collection tool of FIG. 24.
Figure 26:
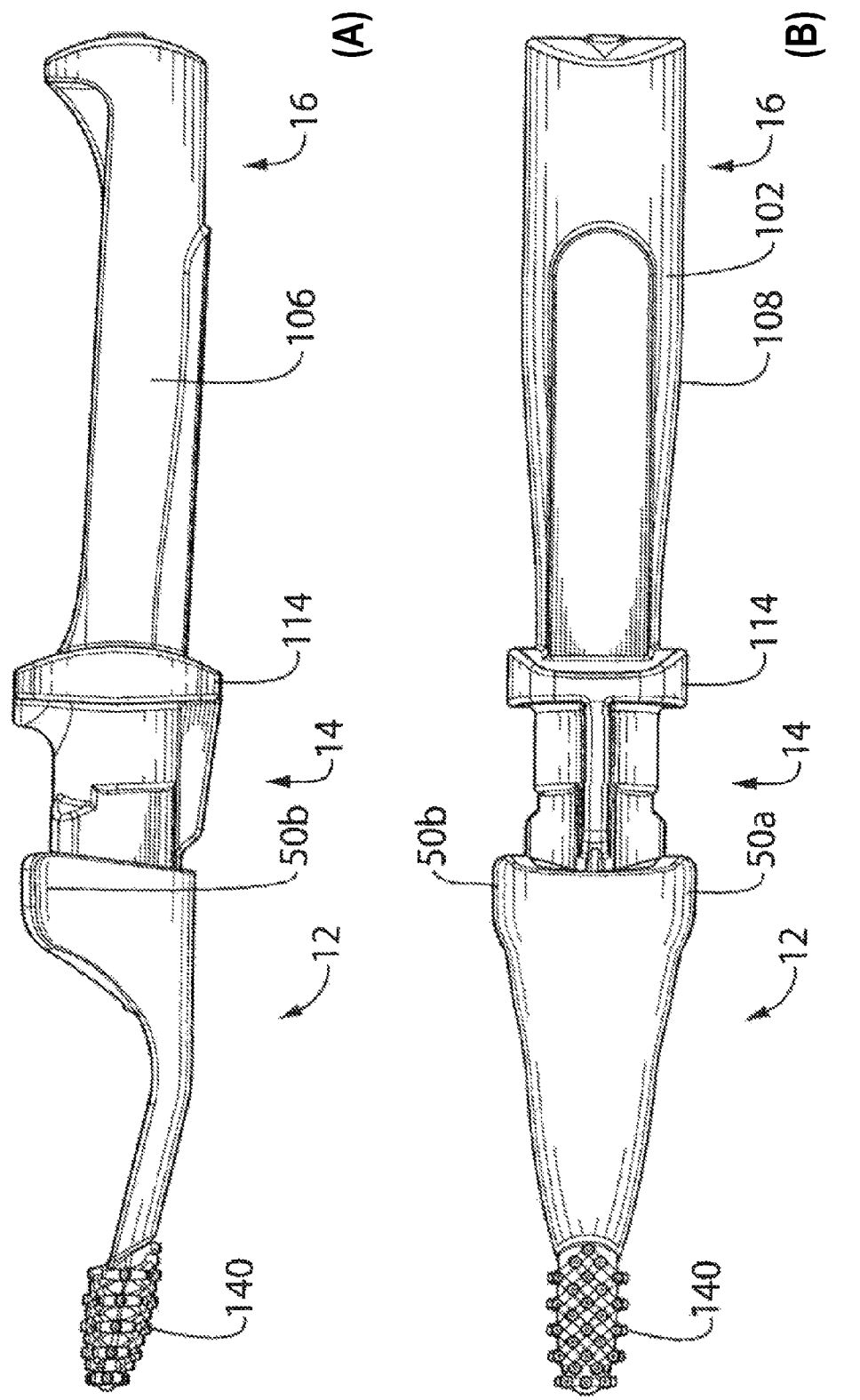
FIG. 26 is a side view (A) and top view (B) of a sample collection device according to one embodiment.

Each collection tool was gently scraped ten times on the inside of one cheek (10×), on the inside of two cheeks, consecutively (20×), or two collection tools (A+B) per mouse were used such that one collection tool (A) was gently scraped ten times on the inside of one cheek and a second collection tool (B) was gently scraped ten times on the inside of the second cheek (10+10×). In addition, either the features (the raised ridges on the convex side) or the scoop (the edge of the spoon) were used for collecting. The collection tool was then left in the stabilizing solution for processing. Each collection tool was placed in a single microcentrifuge tube containing 200 µL stabilizing solution. Total DNA was isolated from each tube, resuspended in either 50 µL TE (10× and 20×) or 25 µL TE (10+10× A/B) and quantified. The data is presented in FIG. 23 as a vertical scatter plot with mean (line)+/− standard deviation. For 10+10×, the DNA was quantified for A and B and the totals added. Collecting either 10× or 20× resulted in comparable amounts of total DNA for both features and scoop (compare column 1 to column 2 and column 6 to column 7). These results suggest that the collection tool is saturated with sample after scraping the inside of animal's cheek 10×, since an increase in sample yield is not observed after scraping the inside of animal's cheek 20×.

In contrast, use of two individual collection tools to collect sample from the same mouse (10+10×) resulted in a higher total DNA yield (see columns 3, 4 and 5). These results indicate that an increased surface area improves overall DNA yield and that a collection tool having raised sampling elements on both faces will facilitate increased sample yield without the need to use two separate collection tools.

Example 3

Figure 33:
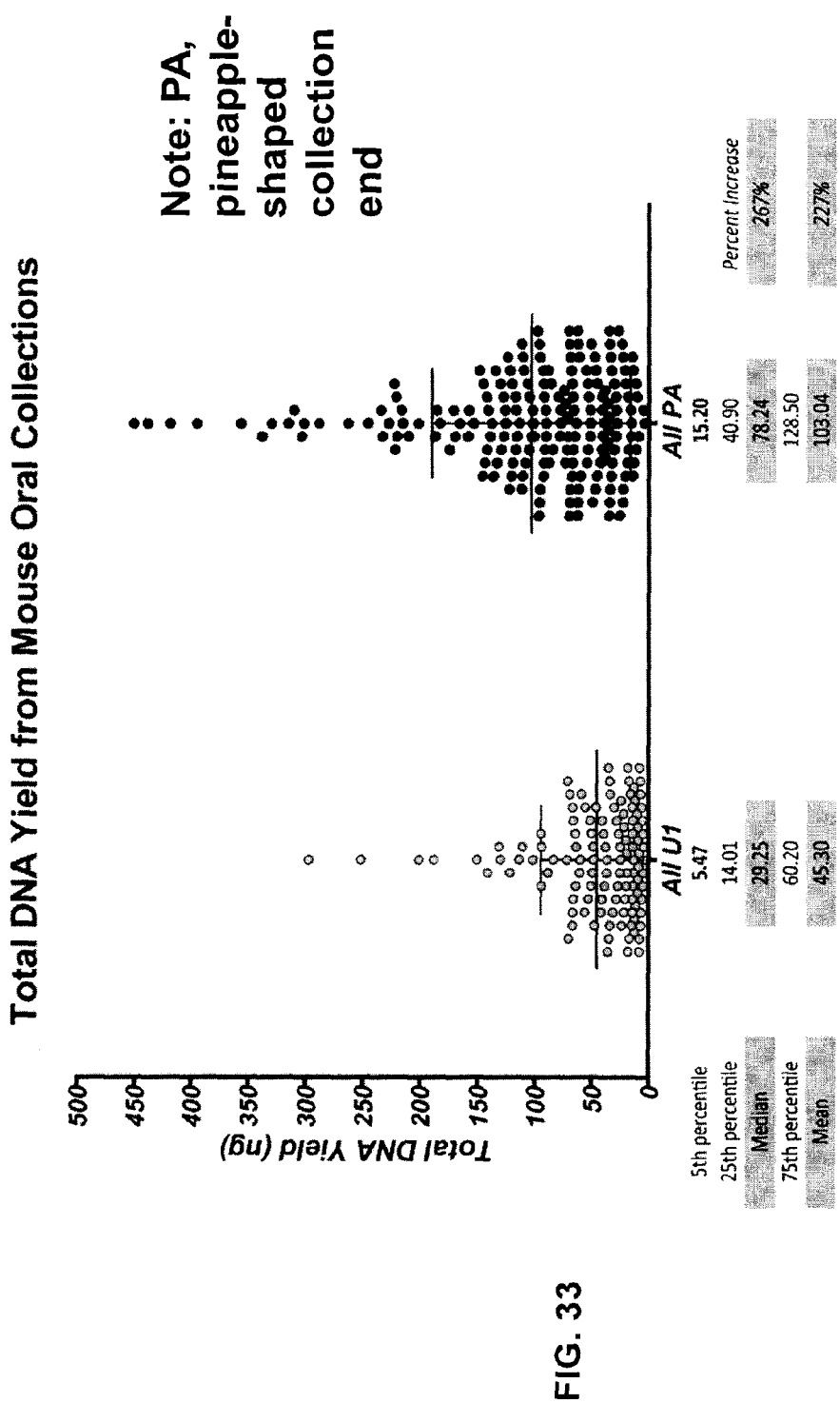
FIG. 33 graphically depicts total DNA yield obtained from mouse oral samples using a prior art sample collection device in comparison to a sample collection device according to one embodiment.

A comparison of total DNA yield from mouse oral collections using the sample collection tool (PA) of the present invention and a scoop-shaped collection device (U1) was performed. As in Example 2, each device was gently scraped ten times on the inside of two cheeks, consecutively (i.e., 20×). The device was then left in the stabilizing solution. As illustrated in FIG. 33, an overall higher total DNA yield was demonstrated with the sample collection tool of the present invention. This may be attributed to an increased surface area of the collection end of the sample collection tool as compared with the scoop-shaped collection device.

Example 4

Figure 34:
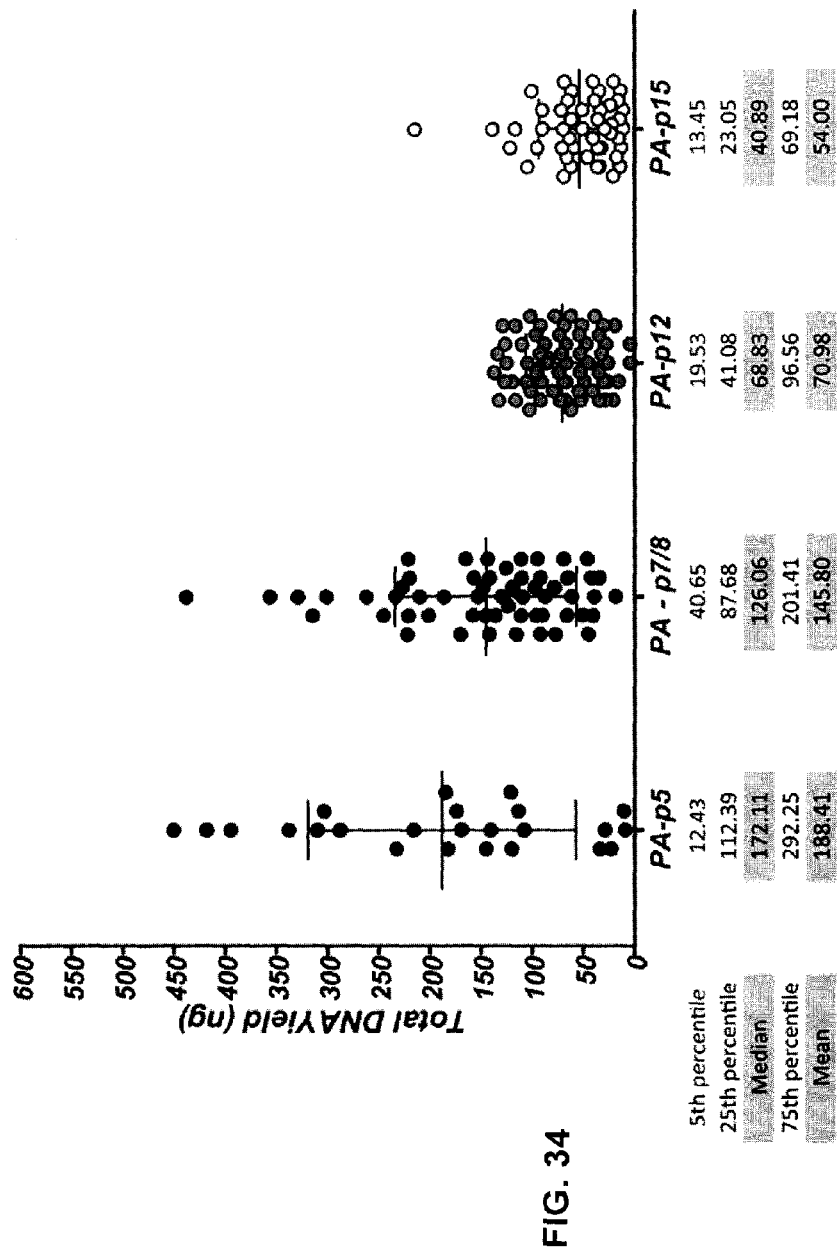
FIG. 34 graphically depicts total DNA yield obtained from p5, p7/8, p12 and p15 mouse pup oral samples using a sample collection device according to one embodiment.

Total DNA yield from pups of different ages was assessed using a sample collection tool of the present invention. Samples of DNA were collected from mouse pups at four timepoints: p (postnatal day) 5, p7/8, p12 and p15. As in Example 2, each device was gently scraped ten times on the inside of two cheeks, consecutively (i.e., 20×). The device was then left in the stabilizing solution. As illustrated in FIG. 34, the mean DNA yield from the mouse pups decreased over time, with the highest yield at p5 and the lowest at p15.

Example 5

Figure 35:
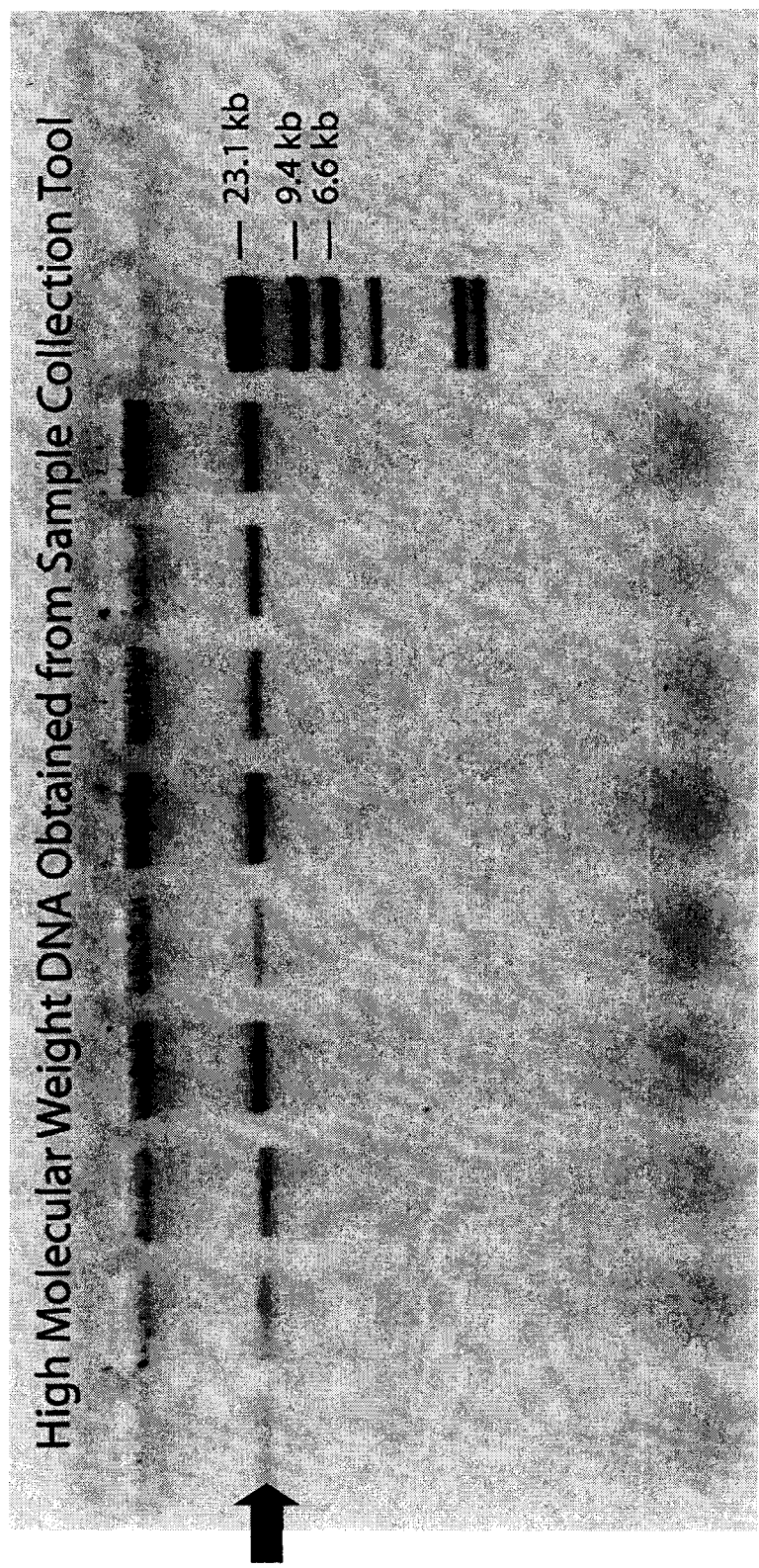
FIG. 35 is an agarose gel of mouse oral cavity DNA collected using a sample collection device according to one embodiment.

Using a sample collection tool of the present invention, DNA was collected from the oral cavities of mice and analyzed for molecular weight. As in Example 2, each device was gently scraped ten times on the inside of two cheeks, consecutively (i.e., 20×). The device was then left in the stabilizing solution. As illustrated in FIG. 35, the sample collection tool allows for the collection of intact, high molecular weight genomic DNA in large enough quantities to be visualized on an agarose gel.

Example 6

Post Processing for PCR
In the vivarium/animal facilities, sterile sample collection tools of the present invention were used to collect oral samples from mice. Samples were placed into thin-walled 200 µL PCR strip tubes pre-filled with 50 µL DNA-preserving solution, such as a solution described in the Applicant's US Patent Application 2009/0123976 entitled "Compositions and Method for Storage of Nucleic Acid From Bodily Fluids" and incorporated herein by reference. These samples can be stored under ambient conditions for several months, prior to analysis. In the genotyping laboratory, five µL of Quick-to-PCR Reagent (herein referred to as a "PCR reagent") was added to each sample tube and the tubes were recapped. The exemplary Quick-to-PCR solution comprised proteinase K, KCl, and $MgCl_2$, for a total sample volume of 55 µL (sample plus DNA-preserving solution plus Quick-to-PCR Reagent).

In a standard PCR thermocycler, samples were incubated as follows: 1) 60° C. for 15-60 minutes (to degrade protein and nucleases in the sample); 2) 90° C. for 15 minutes (to inactive proteinase K); and 4° C. for 10 minutes (to precipitate impurities, such as detergent and protein). An optional step of centrifuging the sample at 5000 rpm for 5 minutes to bring down precipitates was employed; however, it is contemplated that this centrifugation step can be added at the discretion of the user. From this sample, a 2.5 µL aliquot was used directly in a PCR reaction, foregoing the conventional DNA extraction protocol and ethanol precipitation of nucleic acids.

Thus, mice can be non-invasively sampled and genotyped using the device and methods of the present invention in substantially less time than with standard devices and methods known in the art. In ideal situations, the overall method can take only a few hours, compared to typical tail-snip methods which can take several days. Thus, costs for keeping and storing animals can be reduced. Further, the present method permits the collection and analysis of DNA samples from neonatal juvenile mice, removing the need to wait until the mice are 3 weeks old for tissue samples. The reduced wait time can be particularly advantageous, since 3-week-old mice are often about to be weaned. Weaning the mice means separating the pups from the dam into separate cages which translates to increased costs with every litter of mice. Using the tail-snip method, the tail snips are often collected around weaning which delays the genotype results and necessitates the maintenance of extra cages. The extra costs may prove a barrier to the investigator seeking a robust set of genotype data. Conversely, with the present method, mice are sampled earlier, genotype results can be obtained as early as the same day as sampling, and the investigator will know which mice to keep and which mice to cull at weaning. Thus, the present method can provide improved efficiency for generating high quality data.

It is contemplated that any of the steps in the above protocol may be amended or substituted as warranted for the desired end use. For example, the incubation time and temperature in step 1) may be changed to 15 to 30 minutes at 50-60° C., if desired.

Further, the kit may comprise additional tubes for processing the samples which may contain other reagents as required. It is also contemplated that any or all of the reagents may be dried for reconstitution prior to use. For example, a protease (such as proteinase K) may be dried within a collection tube, and dissolved in the remainder of the DNA-preservation solution prior to the addition of the sample on the collection end of the sample tool. Similarly, a protease (such as proteinase K) may be dried in a tube or bottle, and dissolved in the Quick-to-PCR Reagent prior to mixture with the sample/DNA-preserving solution.

Additionally, it is contemplated that the strip tubes could be pre-filled with DNA-preserving gel, slurry, colloidal suspension, viscous solution or soluble matrix. For example, agarose (0.1-1%) or gelatin may be added to the DNA-preserving solution/PCR reagent. A solid or semi-solid DNA-preserving gel may be particularly advantageous during transport of the product. In the genotyping lab, a small volume of Quick-to-PCR diluent would be added to samples comprising proteinase K, KCl and $MgCl_2$. In the thermocycler, the gel would melt and all the reagents would mix. The heating steps may be altered as appropriate. Preferably the sample stays liquid, i.e. does not revert to the gel/semi-solid state, following the addition of Quick-to-PCR diluent and the heating steps. A small aliquot could then be used directly in a PCR reaction.

Modifications and improvements to the above-described embodiments of the present invention may become apparent to those skilled in the art. The foregoing description is intended to be exemplary rather than limiting. The scope of the present invention is therefore intended to be limited solely by the scope of the appended claims.

We claim:

1. A sample collection tool comprising:
   a collection end;
   a first handle portion having a first end connected to the collection end and a second end, the first handle portion having a narrow section towards said first end forming a tip and a wide section towards said second end wherein said narrow section is narrower than said wide section; and
   a second handle portion connected to the second end of the first handle portion by a breakable connection, the second end of the first handle portion having at least one winglet, the at least one winglet being compliant in a preferential direction, the breakable connection being ruptured at least in part when the at least one winglet is forced in the preferential direction.

2. The sample collection tool of claim 1, wherein the first handle portion defines a hollow area for tools to enter proximal to said collection end.

3. The sample collection tool of claim 1, wherein the collection end is ovoid.

4. The sample collection tool wherein said collection end has a plurality of stubs having blunt ends.

5. The sample collection tool of claim 1 wherein said collection end is flattened to define two faces.

6. The sample collection tool of claim 4 wherein said stubs are arranged as a first set of parallel ridges and a second set of parallel ridges.

7. The sample collection tool of claim 4 wherein said stubs are raised ridges arranged in rows.

8. The sample collection tool of claim 1 wherein said collection end has a circular cross sectional area.

9. The sample collection tool of claim 1 wherein said collection end is constructed and arranged to be received in a tube at least 2 mm in diameter.

10. The sample collection tool of claim 1, wherein the collection end is configured for collecting a sample from a body of an animal, a non-animal source, mouth, vagina, rectum, nose, sinus, ear, throat, saliva, buccal cells, mucus, feces, sputum, vaginal secretions, nasal secretions, or soil.

11. The sample collection tool of claim 1, wherein the breakable connection comprises at least two breakable attachment points.

12. The sample collection tool of claim 11, wherein the first handle portion further comprises a pair of protrusions, the pair of protrusions facing a pair of the winglets, and each protrusion of the pair of protrusions is connected to a facing one of the pair of winglets by at least one of the at least three breakable points.

13. The sample collection tool of claim 12, wherein an end of the second handle portion connecting the first handle portion is a closed end and comprises a structural reinforcement for facilitating rupture of the at least three breakable points.

14. The sample collection tool of claim 13, wherein the second end of the first handle portion is an open end to allow a sample withdrawal device to be inserted in the hollow section of the first handle portion; and the first end of the first handle portion is a closed and angularly oriented ribbed surface for preventing the pipette to be blocked.

15. The sample collection tool of claim 13, wherein the collection end and the first handle portion are dimensioned to provoke rupture of breakable points located at the pair of winglets when the sample collection tool is inserted into a PCR or microcentrifuge tube by having inner walls of the tube forcing of the pair of winglets into the preferential direction.

16. The sample collection tool of claim 15, wherein rupture of the at least one breakable point located away from the pair of winglets is eased by abutting the collection end and the first handle portion against the inner walls of the PCR or microcentrifuge tube while moving the second handle portion angularly away from the first handle portion.

17. The sample collection tool of claim 16, wherein the collection end and the first handle portion are dimensioned to fit inside the PCR or microcentrifuge tube, and the tube containing the collection end and the first handle portion is resealable after the second handle portion has been removed from the sample collection tool.

18. The sample collection tool of claim 17, wherein the first handle portion comprises a zone adapted to receive a dried reagent, the zone being located toward the first end of the first handle portion and above the collection end.

19. The sample collection tool of claim 18, wherein the dried reagent is proteinase K.

20. The sample collection tool of claim 18, wherein the collection end is adapted to contact a bottom of the PCR or microcentrifuge tube thereby facilitating contact of the zone receiving the dried reagent when a limited amount of a medium is introduced to the tube.

21. The sample collection tool of claim 1, wherein the sample collection tool has a length of from 2 mm to 25 cm, and wherein the collection end fits into a tube of at least 2 mm in diameter and at least 4 mm in length.

22. A sample collection kit, comprising:
the sample collection tool of claim 1, and
a receptacle for receiving the sample collection tool following collection of a sample.

23. The sample collection kit of claim 22, further comprising:
a container comprising a medium for preserving the sample when the solution is added to the receptacle containing the sample.

24. The sample collection kit of claim 22, further comprising a protease.

25. The sample collection kit of claim 22, wherein the sample comprises a biomolecule.

26. The sample collection kit of claim 22, wherein the sample is a nucleic acid sample and the solution comprises a nucleic acid-preserving medium.

27. The sample collection kit of claim 22, wherein the sample is from a vagina, rectum, nose, sinus, ear, mouth or throat.

28. The sample collection kit of claim 22, wherein the receptacle is a PCR or microcentrifuge tube.

29. The sample collection kit of claim 28, wherein the tube comprises a PCR reagent.

30. The sample collection kit of claim 29, wherein the PCR reagent comprises $MgCl_2$, octylphenol ethoxylate, and KCl.

31. The sample collection kit of claim 22, which further comprises a reagent for extracting a nucleic acid from the sample selected from the group consisting of, a stabilizing medium, a fixative, a solution for preparing the sample for further analysis, a decontaminant, a disinfectant, and a solution for facilitating transport of the sample.

32. A method of obtaining a sample from a subject, comprising:
providing a subject; and
contacting the sample collection tool of claim 1 with the subject such that a sample from the subject is obtained.

33. The sample collection tool of claim 1, wherein the collection end is scoop-shaped.

* * * * *